US012666232B2

(12) United States Patent
Bryant et al.

(10) Patent No.: US 12,666,232 B2
(45) Date of Patent: Jun. 23, 2026

(54) COMMUNICATION MODULE FOR AN AUTOINJECTOR

(71) Applicant: Novartis AG, Basel (CH)

(72) Inventors: Andrew Bryant, Buggingen (DE); Neil Cammish, Manchester (GB); Mark Horlock, Cheshire (GB); John Palmer-Felgate, West Sussex (GB); Claudio Rossi, Elinsbach (CH); Alain Schmidlin, Saint Louis (FR); Rafael Weiler, Basel (CH)

(73) Assignee: Novartis AG, Basel (CH)

( * ) Notice: Subject to any disclaimer, the term of this patent is extended or adjusted under 35 U.S.C. 154(b) by 1206 days.

(21) Appl. No.: 17/554,797

(22) Filed: Dec. 17, 2021

(65) Prior Publication Data

US 2022/0217511 A1    Jul. 7, 2022

Related U.S. Application Data

(60) Provisional application No. 63/127,622, filed on Dec. 18, 2020.

(51) Int. Cl.
| | |
|---|---|
| *H04W 4/38* | (2018.01) |
| *A61M 5/32* | (2006.01) |
| *H04W 4/80* | (2018.01) |
| *A61M 5/20* | (2006.01) |
| *G09B 23/28* | (2006.01) |

(52) U.S. Cl.
CPC ............ *H04W 4/38* (2018.02); *A61M 5/3202* (2013.01); *H04W 4/80* (2018.02); *A61M 5/20* (2013.01); *A61M 2205/14* (2013.01); *A61M*

2205/3368 (2013.01); *A61M 2205/3592* (2013.01); *A61M 2205/60* (2013.01); *A61M 2205/8206* (2013.01);
(Continued)

(58) Field of Classification Search
CPC .. A61M 5/20; A61M 5/3202; A61M 2205/14; A61M 2205/3368; A61M 2205/3592; A61M 2205/60; A61M 2205/8206; A61M 2207/00; H04W 4/38; H04W 4/80; G09B 23/285
See application file for complete search history.

(56) References Cited

U.S. PATENT DOCUMENTS

| | | | |
|---|---|---|---|
| 3,220,412 A | 11/1965 | McConnaughey et al. |
| 5,681,291 A | 10/1997 | Galli |
(Continued)

FOREIGN PATENT DOCUMENTS

| | | |
|---|---|---|
| AU | 2010201665 C1 | 1/2020 |
| AU | 2018202115 B2 | 3/2020 |
(Continued)

OTHER PUBLICATIONS

U.S. Appl. No. 17/057,558, filed Jun. 5, 2025.
(Continued)

*Primary Examiner* — Bhisma Mehta
*Assistant Examiner* — Marissa Taylor
(74) *Attorney, Agent, or Firm* — FBT Gibbons LLP

(57) ABSTRACT

The invention provides a communication module for an autoinjector comprising a detector component configured to detect an injector usage event to obtain injector usage information and a transmitter component configured to wirelessly transmit injector usage information to a receiving device.

14 Claims, 18 Drawing Sheets

(52) U.S. Cl.
CPC ....... *A61M 2207/00* (2013.01); *G09B 23/285*
(2013.01)

(56)                        References Cited

U.S. PATENT DOCUMENTS

| 7,566,322 | B2 | 7/2009 | Brand et al. |
| 8,048,035 | B2 | 11/2011 | Mesa et al. |
| 8,398,594 | B2 | 3/2013 | Streit et al. |
| 8,641,668 | B2 | 2/2014 | Matusch |
| 8,979,807 | B2 | 3/2015 | Grunhut et al. |
| 8,992,477 | B2 | 3/2015 | Raday et al. |
| 9,125,996 | B2 | 9/2015 | Takemoto |
| 9,205,199 | B2 | 12/2015 | Kemp et al. |
| 9,227,017 | B2 | 1/2016 | Buchine et al. |
| 9,265,892 | B2 | 2/2016 | Segal |
| 9,327,084 | B2 | 5/2016 | Evans |
| 9,333,305 | B2 | 5/2016 | McLoughlin et al. |
| 9,522,231 | B2 | 12/2016 | Schneider et al. |
| 9,526,845 | B2 | 12/2016 | Roberts et al. |
| 9,579,459 | B2 | 2/2017 | Jennings et al. |
| 9,579,460 | B2 | 2/2017 | Marshall et al. |
| 9,604,011 | B2 | 3/2017 | Roberts et al. |
| 9,744,306 | B2 | 8/2017 | Cowe |
| 9,757,524 | B2 | 9/2017 | McLoughlin et al. |
| 9,789,253 | B2 | 10/2017 | Fabien et al. |
| 9,789,257 | B2 | 10/2017 | Travanty |
| 9,795,734 | B2 | 10/2017 | McLoughlin et al. |
| 9,821,115 | B2 | 11/2017 | Wozencroft |
| 9,861,751 | B2 | 1/2018 | Iio et al. |
| 9,974,904 | B2 | 5/2018 | Burk et al. |
| 9,999,734 | B2 | 6/2018 | Cowe |
| 10,010,680 | B2 | 7/2018 | Limaye et al. |
| 10,080,846 | B2 | 9/2018 | Sonderegger et al. |
| 10,105,499 | B2 | 10/2018 | Schwirtz et al. |
| 10,137,248 | B2 | 11/2018 | Holmqvist et al. |
| 10,183,121 | B2 | 1/2019 | Cowe |
| 10,188,799 | B2 | 1/2019 | Saussaye et al. |
| 10,207,052 | B2 | 2/2019 | Saussaye |
| 10,220,160 | B2 | 3/2019 | Ruan et al. |
| 10,232,117 | B2 | 3/2019 | Halseth |
| 10,232,124 | B2 | 3/2019 | Cowe |
| 10,238,804 | B2 | 3/2019 | Young et al. |
| 10,238,805 | B2 | 3/2019 | Carmel et al. |
| 10,265,471 | B2 | 4/2019 | Kapas et al. |
| 10,279,130 | B2 | 5/2019 | Mosebach et al. |
| 10,293,120 | B2 | 5/2019 | Cabiri et al. |
| 10,300,218 | B2 | 5/2019 | Stefanov et al. |
| 10,307,539 | B2 | 6/2019 | Alexandersson |
| 10,335,549 | B2 | 7/2019 | Edwards et al. |
| 10,350,362 | B2 | 7/2019 | Dennis, Jr. et al. |
| 10,350,371 | B2 | 7/2019 | Bates et al. |
| 10,363,377 | B2 | 7/2019 | Atterbury et al. |
| 10,384,009 | B2 | 8/2019 | Olson et al. |
| 10,384,015 | B2 | 8/2019 | Brereton et al. |
| 10,391,244 | B2 | 8/2019 | Schweikert et al. |
| 10,391,257 | B2 | 8/2019 | Piehl et al. |
| 10,398,842 | B2 | 9/2019 | Niven et al. |
| 10,406,280 | B2 | 9/2019 | Cronenberg |
| 10,420,898 | B2 | 9/2019 | Daniel |
| 10,420,899 | B2 | 9/2019 | Draper et al. |
| 10,485,933 | B2 | 11/2019 | Vogt et al. |
| 10,518,033 | B2 | 12/2019 | Takabatake et al. |
| 10,518,041 | B2 | 12/2019 | Brereton et al. |
| 10,543,322 | B2 | 1/2020 | Benito et al. |
| 10,583,260 | B2 | 3/2020 | Kemp |
| 11,197,963 | B2 | 12/2021 | Helmer et al. |
| 2009/0118677 | A1 | 5/2009 | Walton |
| 2011/0190693 | A1* | 8/2011 | Takatsuka ......... A61M 5/14546 |
|  |  |  | 340/815.4 |
| 2011/0270161 | A1 | 11/2011 | Harrison |
| 2013/0281938 | A1 | 10/2013 | Ekman |
| 2013/0310746 | A1 | 11/2013 | Wozencroft |
| 2013/0331796 | A1 | 12/2013 | Wozencraft |
| 2014/0025013 | A1 | 1/2014 | Dowds |
| 2014/0135303 | A1 | 5/2014 | Wotton |
| 2014/0343504 | A1 | 11/2014 | Bicknell |
| 2016/0015897 | A1 | 1/2016 | Bui |
| 2016/0317751 | A1 | 11/2016 | Andersen |
| 2016/0331900 | A1 | 11/2016 | Wei |
| 2016/0361496 | A1 | 12/2016 | Guillermo |
| 2017/0065763 | A1 | 3/2017 | Rossitto |
| 2017/0143893 | A1 | 5/2017 | Hasumi |
| 2017/0239424 | A1 | 8/2017 | Wei |
| 2017/0246389 | A1 | 8/2017 | Stillman |
| 2017/0246400 | A1 | 8/2017 | Slobodan |
| 2017/0274150 | A1 | 9/2017 | Takabatake |
| 2017/0354779 | A1 | 12/2017 | Atterbury |
| 2018/0001025 | A1 | 1/2018 | Sarkinen |
| 2018/0036492 | A1 | 2/2018 | Schader |
| 2018/0117264 | A1 | 5/2018 | Hirobe |
| 2018/0161504 | A1 | 6/2018 | Kemp |
| 2018/0169338 | A1 | 6/2018 | Mosebach |
| 2018/0296768 | A1 | 10/2018 | Gould |
| 2018/0339114 | A1 | 11/2018 | Wendland |
| 2019/0001070 | A1 | 1/2019 | Wendland |
| 2019/0009025 | A1 | 1/2019 | Chakrabarti |
| 2019/0009037 | A1 | 1/2019 | Wendland |
| 2019/0022317 | A1 | 1/2019 | Uddin |
| 2019/0046735 | A1 | 2/2019 | Ingerslev |
| 2019/0111214 | A1 | 4/2019 | Gillespie |
| 2019/0151561 | A1 | 5/2019 | Bernhard |
| 2019/0151564 | A1 | 5/2019 | Schrul |
| 2019/0151565 | A1 | 5/2019 | Groetzbach |
| 2019/0160933 | A1 | 5/2019 | Kim |
| 2019/0184093 | A1 | 6/2019 | Sjolund |
| 2019/0184094 | A1* | 6/2019 | Sjolund ............... A61B 5/7405 |
| 2019/0184101 | A1 | 6/2019 | Wendland |
| 2019/0209786 | A1 | 7/2019 | Tschirren |
| 2019/0224416 | A1 | 7/2019 | Dugand |
| 2019/0250070 | A1 | 8/2019 | Fetzer |
| 2019/0282761 | A1 | 9/2019 | Wilson et al. |
| 2019/0282767 | A1 | 9/2019 | Pedersen |
| 2019/0298928 | A1 | 10/2019 | Shaw |
| 2019/0328968 | A1 | 10/2019 | Giamattista |
| 2019/0336700 | A1 | 11/2019 | Nober |
| 2019/0351139 | A1 | 11/2019 | Sarkorov |
| 2019/0374722 | A1 | 12/2019 | Corrigan et al. |
| 2019/0381238 | A1 | 12/2019 | Stonecipher |
| 2020/0009314 | A1 | 1/2020 | Helmer |
| 2020/0023144 | A1 | 1/2020 | Burkett |
| 2020/0030540 | A1 | 1/2020 | Watts |
| 2020/0030547 | A1 | 1/2020 | Wang |
| 2020/0038598 | A1 | 2/2020 | Chu et al. |
| 2020/0046901 | A1 | 2/2020 | Alexandersson |
| 2020/0046907 | A1 | 2/2020 | Schader |
| 2020/0061302 | A1 | 2/2020 | Alexandersson |
| 2020/0078526 | A1* | 3/2020 | Klemm ................... A61M 5/24 |
| 2020/0360615 | A1* | 11/2020 | Helmer ............... A61M 5/3157 |
| 2022/0184320 | A1* | 6/2022 | Helmer .................. G16H 20/17 |

FOREIGN PATENT DOCUMENTS

| BR | PI0815136 | A2 | 2/2015 |
| CA | 2823739 | C | 5/2019 |
| CH | 712459 |  | 11/2017 |
| CH | 714525 |  | 6/2019 |
| CH | 714526 |  | 6/2019 |
| CH | 714527 |  | 6/2019 |
| CH | 714528 |  | 6/2019 |
| CN | 103596612 | A | 2/2014 |
| CN | 104780906 | A | 7/2015 |
| CN | 109331295 | A | 2/2019 |
| CN | 209575432 | U | 11/2019 |
| CN | 209734664 | U | 12/2019 |
| EP | 1044698 | A1 | 10/2000 |
| EP | 1715903 | B1 | 10/2007 |
| EP | 2162170 | B1 | 3/2011 |
| EP | 2438947 | A1 | 4/2012 |
| EP | 2324875 | B1 | 4/2014 |
| EP | 2455124 | B1 | 6/2014 |
| EP | 1755706 | B2 | 12/2014 |
| EP | 2745866 | B1 | 10/2016 |
| EP | 3416706 | B1 | 1/2017 |
| EP | 2903670 | B1 | 4/2017 |

(56) References Cited

FOREIGN PATENT DOCUMENTS

| | | | |
|---|---|---|---|
| EP | 2043711 | A4 | 8/2017 |
| EP | 2680906 | B1 | 11/2017 |
| EP | 2691134 | B1 | 1/2018 |
| EP | 3030287 | B1 | 1/2018 |
| EP | 3468644 | | 4/2019 |
| EP | 2903667 | B1 | 7/2019 |
| EP | 3325051 | B1 | 7/2019 |
| EP | 2023983 | B1 | 8/2019 |
| EP | 3368101 | B1 | 9/2019 |
| EP | 3374008 | B1 | 9/2019 |
| EP | 3541453 | | 9/2019 |
| EP | 3407939 | B1 | 10/2019 |
| EP | 3570913 | | 11/2019 |
| EP | 3446734 | A4 | 1/2020 |
| EP | 3595749 | | 1/2020 |
| EP | 3552642 | B1 | 1/2021 |
| EP | 2918299 | B1 | 9/2021 |
| EP | 2695630 | B1 | 1/2022 |
| EP | 3618904 | B1 | 1/2022 |
| GB | 257031 | | 8/1926 |
| GB | 2493432 | | 2/2013 |
| GB | 2538068 | | 11/2016 |
| GB | 2570319 | | 7/2019 |
| IT | 920120 | | 11/1992 |
| JP | 6456820 | | 1/2019 |
| WO | 94011041 | | 5/1994 |
| WO | 2005070481 | A1 | 8/2005 |
| WO | 2005115508 | A1 | 12/2005 |
| WO | 2006079064 | A1 | 7/2006 |
| WO | 2009007229 | A1 | 1/2009 |
| WO | 2009019440 | A1 | 2/2009 |
| WO | 2009102596 | A1 | 8/2009 |
| WO | 2010007395 | A1 | 1/2010 |
| WO | 2010136076 | A1 | 12/2010 |
| WO | 2011123024 | A1 | 10/2011 |
| WO | 2012085017 | A2 | 12/2011 |
| WO | 2012101629 | A1 | 8/2012 |
| WO | 2012103140 | A1 | 8/2012 |
| WO | 2012117255 | A1 | 9/2012 |
| WO | 2012129174 | A1 | 9/2012 |
| WO | 2012137803 | A1 | 10/2012 |
| WO | 2013012745 | A1 | 1/2013 |
| WO | 2013016832 | A1 | 2/2013 |
| WO | 2013089620 | A1 | 6/2013 |
| WO | 2013152323 | A1 | 10/2013 |
| WO | 2013167494 | A1 | 11/2013 |
| WO | 2013169800 | A1 | 11/2013 |
| WO | 2013169804 | A1 | 11/2013 |
| WO | 2013078771 | | 12/2013 |
| WO | 2013178512 | A1 | 12/2013 |
| WO | 14005955 | | 1/2014 |
| WO | 2014009705 | A1 | 1/2014 |
| WO | 2014053451 | A1 | 4/2014 |
| WO | 2014124427 | A1 | 8/2014 |
| WO | 2014124464 | A1 | 8/2014 |
| WO | 2014146209 | A1 | 9/2014 |
| WO | 2014146210 | A1 | 9/2014 |
| WO | 2015018578 | A1 | 2/2015 |
| WO | 2015075399 | A1 | 5/2015 |
| WO | 2015090320 | A2 | 6/2015 |
| WO | 2015110533 | A1 | 7/2015 |
| WO | 2015113172 | A1 | 8/2015 |
| WO | 2016025327 | A1 | 2/2016 |
| WO | 2016075254 | A1 | 5/2016 |
| WO | 201687187 | A1 | 6/2016 |
| WO | 2016174245 | A1 | 11/2016 |
| WO | 2016177390 | A1 | 11/2016 |
| WO | 2016193343 | A1 | 12/2016 |
| WO | 2016193349 | A1 | 12/2016 |
| WO | 2016193374 | A1 | 12/2016 |
| WO | 2017029032 | A1 | 2/2017 |
| WO | 2017089256 | A1 | 6/2017 |
| WO | 2017186435 | A1 | 11/2017 |
| WO | 2017186472 | A1 | 11/2017 |
| WO | 2017191159 | A1 | 11/2017 |
| WO | 2017191177 | A1 | 11/2017 |
| WO | 2017207224 | A1 | 12/2017 |
| WO | 2017211628 | A1 | 12/2017 |
| WO | 2017223354 | A1 | 12/2017 |
| WO | 2018010947 | A1 | 1/2018 |
| WO | 2018018164 | A1 | 2/2018 |
| WO | 201868959 | A1 | 4/2018 |
| WO | 2018065708 | A1 | 4/2018 |
| WO | 2018077672 | A1 | 5/2018 |
| WO | 2018091257 | A1 | 5/2018 |
| WO | 2018142167 | A1 | 8/2018 |
| WO | 2018167490 | A1 | 9/2018 |
| WO | 2018215270 | A1 | 11/2018 |
| WO | 2018224637 | A1 | 12/2018 |
| WO | 201946436 | A1 | 3/2019 |
| WO | 2019043502 | A1 | 3/2019 |
| WO | 2019058382 | A1 | 3/2019 |
| WO | 201986376 | A1 | 5/2019 |
| WO | 2019126454 | A1 | 6/2019 |
| WO | 2019141573 | A1 | 7/2019 |
| WO | 2019160933 | A1 | 8/2019 |
| WO | 2019179895 | A1 | 9/2019 |
| WO | 2019189278 | A1 | 10/2019 |
| WO | 2019191110 | A1 | 10/2019 |
| WO | 2019224782 | | 11/2019 |
| WO | 2019224783 | | 11/2019 |
| WO | 2019224783 | A1 | 11/2019 |
| WO | 2019224784 | | 11/2019 |
| WO | 2019224785 | | 11/2019 |
| WO | 2019238806 | A1 | 12/2019 |
| WO | 202006751 | A1 | 1/2020 |
| WO | 202015986 | A1 | 1/2020 |
| WO | 2020015985 | A1 | 1/2020 |
| WO | 2020016158 | A1 | 1/2020 |
| WO | 2020023336 | A1 | 1/2020 |
| WO | 2020023444 | A1 | 1/2020 |

OTHER PUBLICATIONS

U.S. Appl. No. 17/057,561, filed Jun. 5, 2025.
U.S. Appl. No. 17/057,562, filed Jun. 5, 2025.
U.S. Appl. No. 17/057,553, filed Jun. 5, 2025.

* cited by examiner

COMMUNICATION MODULE FOR AN AUTOINJECTOR

CROSS REFERENCE TO RELATED APPLICATIONS

This application claims priority to U.S. Provisional Patent Application No. 63/127,622, filed Dec. 18, 2020, all of which is incorporated by reference in their entirety.

The present invention is directed to a communication module for an autoinjector, a reusable communication element for an autoinjector, to an autoinjector comprising a communication module, to a method of manufacturing a component of a medical device, the component comprising a communication module.

Autoinjectors, also sometimes called automatic drug delivery devices, are known examples of medical devices. Such autoinjectors are configured for dispensing a fluid product such as a medicament to a patient. The term autoinjector is used herein to describe not only an automatic drug delivery device described above, but also a training or demonstration device which may be intended to simulate at least some of the functions of such an automatic drug delivery device.

Examples of such autoinjectors for drug delivery are described, for example, in WO 2019/224782, WO 2019/224783, WO 2019/224784 and WO 2019/224785, the contents of which are incorporated herein by reference.

In general, such autoinjectors provide reliable functioning and may be used accurately even by non-experienced persons. Nevertheless, there is still the risk to accidentally inject only part of the dose. Furthermore, some medicaments have to be delivered at certain times of the day and/or at certain intervals.

The invention provides a communication module, a drive module, an autoinjector, a reusable communication element, a method of using an autoinjector and a method of manufacturing a medical device as set out in the attached claims.

The communication module for an autoinjector according to the invention comprises a detector component configured to detect an injector usage event to obtain injector usage information and a transmitter component configured to wirelessly transmit injector usage information to a receiving device.

In this way, it is possible to transmit information about injector usage, in particular, an injection process, to some receiving device which may be, for example, a mobile phone, e.g. the smartphone of a user, a laptop, tablet computing device, personal computer, or other device. Injector usage information is obtained or acquired via the detector component. Since the communication module comprises a detector component which detects an injector usage event as well as a transmitter component as described, monitoring the use of the autoinjector is achieved in a reliable and simple way. The information about injector usage may be additionally or alternatively be used to provide feedback to a user to train or assist a user in the correct use of such a device. The feedback may be provided by the device, or by a companion or linked device such as a mobile phone, personal computer, tablet or other computing device. The feedback may be provided during use of the device with no, or very small time delay, to reflect the actual use of the device at the time, or the feedback may provide feedback after use to improve subsequent use of the same, or a similar, device. The feedback may comprise indications of the state of the autoinjector, for example via an animation or other visual representation, through a text or symbolic indication, a countdown to a next usage step, or a prompt to take a next step. The feedback may comprise an indication relating to correct use of the autoinjector, for example a light may indicate when the device is held at, or is not held at, a predetermined angle.

The detector may be configured to detect particular usage information. The usage information may include an indication that a cap of an autoinjector with which the communication module is associated has been removed. The usage information may include an indication of the usage state of an autoinjector with which the communication module is associated based on the position of elements of a drive mechanism of that autoinjector, for example a trigger element and/or an indicator element. The usage information may include one or more of device orientation before use, device orientation during use, time of use, date of use, temperature of the device and timing of operation of one or more components of the autoinjector.

When the communication module is intended to provide usage information about an autoinjector, the communication module may be arranged in a rear portion of the device. The rear portion being opposite the injection end of the device. The communication module may be arranged so that it is arranged on, or in a rear half of the autoinjector. The communication module may be arranged so that it does not extend towards a front, or injection end of the device, beyond half the length of the device.

The usage information may include information about a condition of the autoinjector, for example a condition that may be indicative of storage quality. A condition of the autoinjector may be monitored continuously or at intervals, regular or irregular, for example from final assembly to use, or during any suitable time period. This time period may include, for example a period of shipping or transporting the autoinjector during which conditions may be more difficult to control. The condition may include temperature and/or agitation. Temperature may be monitored by a temperature sensor and agitation may be measured by an accelerometer. The usage information may comprise an indication regarding whether a quality threshold has been passed, for example a maximum or minimum temperature or level of agitation. The usage information may include an indication of the time for which a particular threshold has been passed. Such condition monitoring may not be appropriate, for example for a training, or demonstration device, which does not contain any medicament.

The communication module may comprise a data storage component to store usage information relating to one or more injector usage events and may be configured to store the usage information for later transmission. The data storage component may comprise a memory. The memory may include non-volatile memory so that the memory content of the non-volatile memory is retained when the memory is not powered by a power supply.

The communication module may comprise a receiver component to receive signals and or data from an external source, for example from the receiving device. This may allow two way communication between the autoinjector and the receiving device. The receiver component may be combined with the transmitter component in the form of a transceiver component. Unless specifically excluded, references to a transmitter component herein include references to a transceiver component.

The transmitter component may be configured to automatically transmit the injector usage information upon creation of that information or to transmit the injector usage information upon receipt of a trigger signal, for example, a trigger signal indicating completion of use of the device, or a trigger from the receiving device and/or a user. The data and/or trigger signal may be transmitted in an encrypted form.

The transmitter component may be configured to transmit injector usage information at a predetermined time. For example, it may transmit injector usage information immediately when (new) injector usage information has been obtained or acquired by the detector component; in other words, it may transmit injector usage information upon detecting an injector usage event, for example any new injector usage event, or a predetermined set of new injector usage events. A set of new usage events may be a set including a cap removal event, which may activate certain components of the communication module, and a dose completion event.

The transmitter component may be configured to wirelessly transmit the injector usage information upon completion of the injection process.

The transmitter component may be configured to automatically transmit injector usage information before, during and/or after use of the autoinjector to train a user, or assist a user, in use of the device.

The detector component may be configured to obtain an injector usage signal upon detection of an injector usage event. Such an injector usage signal may be used in an advantageous way to provide injector usage information. The injector usage signal may directly constitute the injector usage information; alternatively, it may be processed to obtain injector usage information.

The detector component may be configured to detect acoustical, electrical, magnetic, optical, orientation, and/or acceleration signals and/or to detect proximity and/or contact with one or more components. In this way, a reliable detection for obtaining injector usage information is ensured. Such a detected signal may constitute an injector usage signal and/or injector usage information. Alternatively, it may trigger providing and/or generating an injector usage signal and/or injector usage information. The detector component may comprise a contact sensor or a non-contact sensor to detect an electrical, magnetic, acoustical, optical, orientation and/or acceleration signal and/or to detect proximity, contact and/or temperature.

The detector component may comprise a sensor, in particular, an electrical sensor (sensing an electrical signal or an electromagnetic field), such as an inductive sensor or a capacitive sensor, a magnetic sensor (sensing a magnetic flux), such as a Hall sensor which can act as a proximity sensor, an optical sensor, such as a photodetector, an acoustical sensor, such as a microphone, a contact sensor such as an electromechanical mechanical switch, an orientation sensor such as a gyroscope, for example a MEMS gyroscope and/or an acceleration sensor, such as an accelerometer. The orientation sensor and/or acceleration sensor may be configured to detect orientation of the device. Such elements are readily available and allow for a simple and cost-effective configuration of the communication module.

The detector component may comprise two or more sensors. The two or more sensors may be of the same or of different types.

As suggested above, the detector component may comprise a switch, wherein operation (activation, or a state change) of the switch and/or a predetermined switch position is representative of an injector usage event. Via the switch, an electrical signal constituting an injector usage signal may be provided.

The switch may be configured and/or arranged to take at least two switch positions, for example the switch may be movable from a first position to a second position through contact with a component of an autoinjector with which it is associated. At least one switch position being representative of an injector usage event. The detector component may be configured to detect a switch position of a switch.

The switch may be a contact switch, in particular, an electromechanical switch, or a non-contact switch, in particular, a Hall effect switch. The switch may comprise a sensor, in particular, one of the sensors listed above. A non-contact switch enables, or facilitates a water-proof configuration of parts of, or the complete, autoinjector.

The detector component may comprise two or more switches. The two or more switches may be of the same or of different type. In case of two or more switches, operation of two or more of said two or more switches and/or a predetermined switch position two or more of said two or more switches may be representative of an injector usage event. In other words, a combined operation of two or more switches and/or a combination of two or more switch positions may be representative of an injector usage event.

In the above-described communication modules, the communication module and / or the detector component may comprise a main board, for example a printed circuit board with a microcontroller and/or digital signal processor (DSP), or other processor, wherein the microcontroller and/or digital signal processor (DSP), or other processor is configured to process a sensor signal and/or a switch signal. The sensor signal may result from a sensor as described above. The microcontroller and/or digital signal processor (DSP), or other processor may comprise multiple component and be provided in a single, integrated component. The switch signal may result from a switch as described above.

The communication module may also include a component including a memory containing instructions which can be interpreted by a processor of the communication module. As set out above the memory may comprise non-volatile memory. The main board may carry one, some or all of a processor, detector component, power supply, transmitter component and component comprising a memory.

The microcontroller and/or DSP, or other processor may be configured to process a sensor signal and/or a switch signal to obtain an injector usage signal or injector usage information. The microcontroller and/or DSP may be configured to process an injector usage signal to obtain injector usage information.

The microcontroller and/or digital signal processor (DSP), or other processor may be configured to acquire the timing of a detected injector usage event and/or between detected injector usage events. For example, the microcontroller and/or digital signal processor (DSP), or other processor may have a timer, e.g. which can log time difference.

An injector usage event may be one of:
  an injector storage event, in particular, the quality profile over time of the autoinjector since assembly, for example the temperature profile or agitation profile over time;
  an injection preparatory event, in particular, uncasing the autoinjector and/or removal of a cap of the autoinjector, but this could include other preparatory events such as preparatory handling such as mixing components, for example components of the medicament within the device, priming, shaking or resting the device, and/or warming or cooling the device, orienting the device prior to injection; and an injection event, in particular, placement of the autoinjector onto an injection site, start of movement of an injection needle towards puncture, start of dispensing a fluid product, completion of dispensing a fluid product, removal of the autoinjector from an injection site, the orientation of the device during injection, the time between detection of selected actions, the hold time following injection before the autoinjector is removed from the skin.

As noted above, an injector storage event may comprise recording data from one or more sensors prior to the device being used, or being prepared for use, for example prior to removing a cap from the device. In such an example any sensor or element in the detector element used for detecting the injector storage event may be enabled and/or powered following assembly. In some examples the communication module may be in a low power mode in which other sensors or elements that are not used for detecting the injector storage event may be disabled and/or unpowered prior to a particular event, for example an injection preparatory event such as removing a cap from the autoinjector, which may trigger activation of some or all of those sensors as the communication module transitions to a use mode. At least one sensor or detection element may be enabled, or powered following assembly to detect the particular event and thus trigger a change of mode and/or activation of other elements.

The indication of orientation may comprise an indication regarding whether the device was used in a vertical or horizontal orientation. An incorrect usage state may be indicated to a user if the device is not substantially horizontal or vertical prior to use, or when used. A correct usage state may be indicated to a user if the device is substantially horizontal or vertical prior to use, or when used. The correct or incorrect usage state may be indicated to the user by the autoinjector device and/or a linked device. The correct or incorrect usage state may depend upon a selected injection site. For example, a correct usage stage for an injection into the stomach it may be a substantially horizontal autoinjector orientation. As another example, a correct usage state for an injection into a thigh may be a substantially vertical autoinjector orientation. The intended injection site may be indicated by a user providing an input to the autoinjector and/or the receiving device. This may enable the autoinjector or the receiving device to provide feedback and/or guidance to a user regarding use of the device. The detection of orientation of the device may be initiated, activated or enabled by a preparatory event being detected, for example the removal of a cap of the autoinjector.

Useful injector usage events to reliably monitor use of an autoinjector may include, but are not limited, to injector usage events described herein. For example, a start of dispensing a fluid product may be defined by start of movement of a drive mechanism for dispensing the fluid product, e.g. start of movement of a plunger of the autoinjector. Completion of dispensing a fluid product may be defined by end of movement a drive mechanism for dispensing the fluid product, e.g. end of movement of a plunger of the autoinjector. Completion of dispensing a fluid product may trigger a completion indicator event, such as displacement of a completion indicator element. In such a case, detecting the injector usage event of completion of dispensing a fluid product may comprise detecting a completion indicator event, in particular, detecting displacement of a completion indicator element. Completion of a stage of use of the autoinjector may trigger an indicator event, such as displacement of an indicator element. In such a case, detecting the injector usage event of completion of that stage of use of the autoinjector may comprise detecting a completion indicator event, in particular, detecting displacement of a completion indicator element. The indicator element may also be an element that moves to provide an indication which can be sensed by a user, such as a visual, audible or tactile indication.

The detector component may be configured to detect (occurrence of) one or more such indicator usage events. The detector component may be configured to record, at least temporarily, (occurrence of) one or more such indicator usage events For example, the detector component may comprise three switches, i.e. a first switch, a second switch and a third switch. Activation of the first and the third switch, the second switch being deactivated, may be representative of the event of removal of a cap of the autoinjector, activation of the second and the third switch, the first switch being deactivated, may be representative of the event of start of dispensing a fluid product, activation of the second switch, the first and third switch being deactivated, may be representative of the event of completion of dispensing a fluid product, activation of the first switch, the second and third switch being deactivated, may be representative of the event of removal of the autoinjector from an injection site.

In some examples, two of the switches may be configured to detect movement of a trigger element of a drive mechanism of an autoinjector, and one may be configured to detect movement of an injection complete indicator element. The three switches may be arranged in the communication module so as to be distributed along a longitudinal axis of an autoinjector to which the communication module is coupled.

Of course, different numbers of switches and/or different combinations of switch activations and/or deactivations and/or switch positions may be used as well.

Some or all of the switches may be contact switches and/or some or all of the switches may be non-contact switches. For example, the above-described switches may all be Hall effect switches or may all be electromechanical switches, for example contact switches.

In the above-described communication modules, the transmitter component may be configured for transmission via Bluetooth, WLAN, LPWAN, RFID (e.g., Near Field Communication (NFC)) or mobile communications networks.

The particular choice of a transmission hardware and/or protocol may depend on the intended receiving device.

For example, BLE (Bluetooth Low Energy) may be used. This is particularly advantageous as regards power efficiency. Furthermore, due to its short-range capabilities, the risk of intercepting the transmitted signals is reduced. Furthermore, most mobile phones are equipped with Bluetooth receivers, thus, are enabled to communicate with the communication module without additional equipment. As an alternative example, Near Field Communication (NFC) may be used.

The above-described communication modules may comprise a temperature sensor. The transmitter component may be configured to wirelessly transmit temperature information to a receiving device.

Temperature information may constitute an indication whether the autoinjector is ready for use and, as set out above, may also indicate whether the autoinjector has been stored appropriately. For example, the transmitter component may be configured to wirelessly transmit an indication that a fluid product in the autoinjector has a temperature above a predetermined lower threshold and/or below a predetermined upper threshold which may indicate that the device is ready to use, for example the device may need to be stored at a reduced temperature and then warmed to room temperature prior to use Alternatively or additionally, as set out previously, temperature information may be used as a basis of warning information in case the autoinjector has passed a pre-determined temperature threshold during storage or shipping to generate a warning on the receiving device or on the communication module. Passing a pre-determined temperature threshold during storage or shipping may indicate that a quality of a medicament within the autoinjector may be compromised.

The temperature sensor may be a temperature sensor of a processor, digital signal processor or a microcontroller being part of the detector component.

The communication module may comprise a connection component for connecting the communication module to an autoinjector. This allows to retrofit already existing (standard) autoinjectors with such a communication module in a simple way.

The connection component may be configured to provide for an adhesive connection, a frictional connection or a form-fit connection. For example, the attachment component may comprise an adhesive coating. The adhesive coating may be covered by a removable film. Alternatively, the attachment component may comprise a sleeve, a clamp and/or a snap-fit element.

The connection component may be configured for a connection, in particular, an attachment, which is releasable in a non-destructive or a destructive way.

A destructively releasable connection provides for secure connection, whereas a non-destructively releasable connection enables reuse of the communication module. In case the connection component is destructively releasable attached to the autoinjector, it may be disposed of with the autoinjector.

The communication module may be configured to be arranged within a housing of an autoinjector to thereby allow the creation of an autoinjector with an integrated communication module rather than an autoinjector with an external add-on communication module.

At least some of the communication module, for example some, or all, of the electronic components may be removable from the autoinjector after use. This may allow the electronics to be separated from mechanical components of the autoinjector to facilitate disposal and/or recycling.

The communication module may be secured to the autoinjector, or a part thereof, by a frangible connection. The autoinjector may include a releasable connection or catch which secures the communication module to the autoinjector, or a part thereof. The releasable connection or catch may be moved or released during or after use of the autoinjector to allow at least some of the communication module to be more easily removed from the autoinjector.

The communication module may be located so that it is accessible via an opening in a wall of the autoinjector housing. This may facilitate installation and/or removal of the communication module. The opening in the wall of the housing may be covered by an openable or removable portion, such as a door, which can be moved from a closed position to an open position. When in the closed position, the removable portion may cover all, or some, of the opening and may prevent access to the communication module. When in the open position access to the communication module is not prevented by the openable or removable portion and it may be possible to install, access, or remove the communication module via the opening. The communication module may be coupled releasably, or permanently, to the openable or removable portion to be movable therewith so as to facilitate removal of the communication module from the autoinjector. The coupling or couplings between the openable or removable portion may be located anywhere suitable, for example they may be located at, or adjacent a perimeter of the openable or removable portion, at one, or both, opposed axial ends of the openable or removable portion and/or may be at one, or both, opposed lateral sides of the openable or removable portion. The openable or removable portion may be held in place by one or more breakable connections so that it must be destructively opened or removed. The breakable connection may be provided by a molded weakness, a frangible connector, a sticker or label, or other suitable connection. The openable or removable portion may additionally or alternatively be held in place by one or more releasable connections such as catches or latches. A releasable connection may release the openable or removable portion from at least a part of the housing in a non-destructive manner. The openable or removable portion may be held in place by a releasable coupling to a component of the drive mechanism, for example an indicator element.

The openable or removable portion may include gripping portions, which may include, for example slots, indents or other features to facilitate automatic handling of the openable or removable portion, for example during assembly.

Moving the openable or removable portion from the closed position to the open position may comprise breaking one or more breakable connections and/or releasing one or more releasable connections to allow the openable or removable portion to be removed from the housing, or the openable or removable portion may remain attached to the housing for example by a pivot, hinge or tether which allow the openable or removable portion to expose the opening.

The opening in a wall of the housing may be through a wall which extends substantially parallel with the longitudinal axis of the autoinjector. Installation and/or removal of the communication module via the opening may be through movement of the communication module in a direction substantially perpendicular to the longitudinal axis of the autoinjector. This may reduce a likelihood of accidental removal of the communication module, for example when a user is seeking to remove a cap element by applying a pull force along the longitudinal axis.

A releasable connection or catch may be provided on a movable component of the autoinjector, for example an indicator element which provides an indication of a state of the autoinjector. Movement of the movable component may move the catch to release a connection between the communication module and autoinjector and/or between the openable or removable portion and autoinjector.

A portion of the communication module and/or the openable or removable portion may be releasably secured to a component of the drive mechanism. The component of the drive mechanism may secure the communication module and/or the openable or removable portion to the drive mechanism when in an initial position prior to use of the drive mechanism and may move during use of the drive mechanism to release at least a portion of the communication module.

The communication module may comprises a main board and the main board may comprise a board feature, for example a slot, projection, extension or other feature. The openable or removable portion may comprise a door feature, for example a slot, projection, extension or other feature. The component of the drive mechanism may include one or more component features, for example an opening, recess, projection or other feature to engage with the board or door feature. When engaged with the board or door feature the component feature may secure the communication module or openable or removable portion to the drive mechanism. Movement of the component during use of the drive mechanism may move the component feature out of engagement with the board or door feature, thereby releasing the communication module or openable or removable portion from the drive mechanism.

The above-described communication modules may comprise a battery, capacitor or other electrical power source for powering the detector component and/or the transmitter component. The communication module may comprise a recharge component, for example a battery recharge component. In this way, a rechargeable power source, such as a battery may be used. This is particularly useful for a reusable communication module. The battery may be replaceable. The battery may be inserted into and/or removed from the communication module through an opening, for example a slot. The opening or slot may be covered by a door which is openable, for example movable or removable to allow access to the opening or slot.

The above-described communication modules may comprise an activation mechanism to activate or enable the detector component, or elements thereof, a DSP, controller, microcontroller, processor and/or the transmitter component. Such an activation mechanism reduces energy consumption as long as the autoinjector is not in use. For example, the detector component and/or the transmitter component may be in a standby state and are woken up or enabled by the activation mechanism. As another example, the detector component and/or the transmitter component may be disconnected from a power source, and activation by the activation mechanism comprises connecting the detector component and/or transmitter component to the power source and/or powering it up.

The activation mechanism may activate or enable the respective component in a mechanical and/or an electronic way. The activation mechanism may activate the respective component via a switch, such as a contact or a non-contact switch.

The activation mechanism may be configured to establish electrical contact between the battery and the detector component and/or the transmitter component, e.g. when the autoinjector is put into operation. For example, the activation mechanism may comprise a sheet of insulating material between the battery and one or more of its electrical contacts. The sheet may be removed when the autoinjector is put into operation. The activation mechanism may comprise a sensor, such as a switch, which is actuated upon a predetermined event indicative of putting the injector into operation, such as the removal of a cap of an autoinjector. When the predetermined event is detected the communication module may trigger the activation or enabling of other elements of the communication module.

Putting the autoinjector into operation may be defined by one or more predetermined events. For example, the autoinjector may be put into operation by uncasing it/taking it out of its package. In this case, a sheet of insulating material which is arranged between the battery and one of the electrical contacts may be connected to the package so that removing the autoinjector from the package pulls the sheet out of the communication module from between the battery and the electrical contact.

Alternatively, putting the autoinjector into operation may be defined by removing a cap of the autoinjector. Detection of this event may activate or enable the detector component and/or the transmitter component. Detection of the event may be through detection of movement of a component within the drive mechanism of an autoinjector to which the communication module is coupled. The component may move towards an injection end of the autoinjector when the cap is removed. For example, removal of the cap may allow a safety shield to extend from the autoinjector, the component that moves may be a trigger element to which the needle guard is coupled.

As a further alternative, putting the autoinjector into operation may be defined by attaching a communication module to an autoinjector. Detection of this event may activate the detector component and/or the transmitter component. This is particularly useful in case of a reusable or retrofit communication module.

The activation mechanism may comprise a switch to activate or enable the detector component and/or the transmitter component. The switch may be a contact or a non-contact switch. The switch may be configured to switch (operate) upon occurrence of a predetermined event. The predetermined event may be one of the events described above, i.e. uncasing the autoinjector/taking it out of its package, removing a cap of the autoinjector and/or attaching a communication module to an auto-injector.

The invention further provides an autoinjector comprising a communication module as described above.

The autoinjector may be configured as described, for example, in one of the references mentioned above.

For example, the autoinjector may comprise a longitudinal housing extending along a longitudinal axis and having a proximal end close to a dispensing/injection site, a distal end opposite to the proximal end and a hollow interior; a removable cap mountable to the proximal end of the housing; a syringe assembly arranged at a mounting position inside the housing and having a hollow syringe body and an injection needle formed within the hollow syringe body including the fluid product; a drive mechanism which can be triggered by a trigger element in order to initiate dispensing of the fluid product, wherein the drive mechanism is operatively coupled with a safety shield movable within the longitudinal housing, wherein the safety shield is biased into a proximal position in which it protrudes out of the proximal end of the longitudinal housing in order to cover a needle tip of the injection needle, and wherein the safety shield is movable into a distal position in which the injection needle is exposed for injection.

The drive mechanism may include a plunger which may be biased by a drive spring into proximal direction. The plunger may act on a stopper sealably guided within the syringe body and acting on the fluid product included within the syringe body. The syringe holder may receive axial forces applied by the plunger onto the syringe body and may transmit the forces to the longitudinal housing.

The communication module may be mounted to the autoinjector in a non-destructively releasable way or in a destructively releasable way. The communication module may be mounted within the housing of the autoinjector. In this case, the autoinjector may be equipped with a communication module from the beginning, i.e. the point of manufacture.

The invention further provides a demonstration or training autoinjector comprising a communication module as described above. As set out above, a demonstration/training autoinjector may differ from a drug delivery autoinjector in that it may not comprise a syringe and/or no fluid product. Instead of a syringe, it may comprise a surrogate syringe, such as a surrogate syringe without a needle. A training or demonstration autoinjector may provide feedback to a user regarding use of the device, for example feedback regarding correct use, incorrect use or how to improve future use. The feedback may be provided on the autoinjector itself, or via a receiving device which may receive usage information from a communication module which is coupled to the autoinjector.

The invention also provides a reusable communication element for an autoinjector, comprising a communication module as described above and a sleeve for mounting onto the autoinjector. In this way, existing or standard autoinjectors may be equipped with a communication module in a simple way. The sleeve may be configured so as to slip it onto the autoinjector. The sleeve may be configured to partially or fully cover and/or embrace the autoinjector. This allows for a simple connection and attachment of the communication module to the autoinjector.

The reusable communication element is equally suitable for a demonstration/training autoinjector.

The reusable communication element may comprise an autoinjector identifying component configured to acquire identification information from the autoinjector. The identification information may represent information on the autoinjector, for example whether the autoinjector is a training or demonstration device, whether the autoinjector is a medicament delivery device and/or information on the (fluid or powder) product/drug contained therein. In this way, transmitted injector usage information may be linked to a specific autoinjector and/or the product/drug, etc.

The autoinjector-identifying component may comprise a non-contact sensor, in particular, an optical, magnetic and/or electrical sensor. The sensor may be configured to acquire identification in-formation from the autoinjector. As an example, the autoinjector-identifying component may comprise a near field communication (NFC) or RFID reader to read identification information from the autoinjector.

In case of a reusable communication element, the auto-injectors may be equipped with an RFID chip containing an identification of the autoinjector, the drug (product, batch, etc.), an expiry date and/or any other useful information. This data is read by a corresponding reader on the side of the communication module. Alternatively, an NFC reader may be provided for reading out such data.

The reusable combination element may comprise a memory for storing acquired identification information from the autoinjector and/or acquired injector usage information. This allows for transmitting the information/data at a later stage.

The invention provides a method of manufacturing a component for a medical device, the component comprising a communications module, and the method comprising:

a) assembling a preliminary assembly comprising a main board, power source, processor, a detector component configured to detect an usage event to obtain usage information, and a transmitter component configured to wirelessly transmit usage information to a receiving device, the main board comprising at least one component having a memory which includes a first set of instructions;

b) using the processor to run the first set of instructions, the first set of instructions causing the processor to put the communication module into a test mode for a test period and then into a pre-assembly mode, wherein, in the test mode the detector component and the transmitter component are enabled to allow preliminary testing of the component function, and in the pre-assembly mode the detector component is disabled or the transmitter component is disabled;

c) altering the memory of the pre-assembly mode communication module such that that the instructions therein comprise a second set of instructions;

d) using the processor to run the second set of instructions, the second set of instructions causing the processor to put the communication module into an assembly mode in which the detector component is enabled and, upon detection of a usage event, the processor changes the communication module into a use mode in which the detector component and the transmitter component are enabled.

The preliminary assembly provides at least the communication module, and the communication may be as described herein. The preliminary assembly may comprise a component of a medical device, for example a drive mechanism or a housing of an autoinjector. The preliminary assembly may comprise a medicament container, for example a syringe, cartridge, or other container. The preliminary assembly may be a drive module for an autoinjector comprising a communication module and a drive mechanism. The preliminary assembly may be a housing module for an autoinjector comprising a communication module, a housing and a medicament container.

Enabling the detector and/or the transmitter may comprise enabling the detector and/or the transmitter using a software instruction and/or providing power to the component to allow, or cause, it to function. It should also be noted that enabling the detector and/or transmitter includes enabling at least some of the components that comprise the detector and/or transmitter.

This method allows the preliminary module to be tested using the power supply after assembly with the communication module in test mode before the communications module effectively shuts down, or is disabled, to preserve the power supply as instructed by the first set of instructions. Once the preliminary assembly is ready to be installed into or onto a medical device, for example in a device assembly process, the memory can be altered so that it comprises a second set of instructions which cause the communications module to enter an assembly mode, which is a low power mode, in which the detector component is enabled, or powered (but the transmitter component may not be enabled, or powered) and is able to cause the communications module 'wake' and enter a use mode when a usage event is detected.

This method allows power use to be controlled following post-assembly testing of the preliminary assembly so that the preliminary assembly can be stored or transported prior to final assembly into or onto a medical device. This may allow a power supply, for example a battery, of a reduced physical size to be used than might be required if the instructions were not altered prior to final assembly. This may be particularly useful for a disposable medical device which is intended to be disposed of following a predetermined number of uses, for example a single use medicament delivery device.

The method may include put the communication module into a drain mode in which the energy of the power source is used to drain the power source. This may reduce a risk of shorting of the power source. Shorting of the power supply may occur as a result of damage or other fault and may occur, for example, during disposal or storage. Shorting of the power source may result in temperature increase and may result in an increased fire risk.

In the drain mode, the energy of the power source may be used to power one or more components in an inefficient manner, for example continuously operating the transmitter component at high, or full power, or passing current through one or more ballast resistors. The use of the energy of the power source may be controlled to avoid, or reduce a risk of, overheating of the power source, or component being powered.

A drain mode may be triggered following use of the autoinjector, for example completion of an injection and transmission cycle in a single use autoinjector. A drain mode may be triggered by detection of the removal of the communication module from the autoinjector.

The medical device for which the communication module is intended may be any suitable medical device the use or operation of which is to be monitored. The medical device may be a medicament delivery device operable to deliver a medicament to a patient, or to simulate such a device. The medical device may be an autoinjector, for example a single use disposable autoinjector.

The instructions may be altered by updating the firmware of the component, by flash-updating the component. Altering the instructions may involve no hardware changes to the electronics components of the communications module which may prevent the introduction of new hardware problems following preliminary testing. The second set of instructions may replace some or all of the first set of instructions, or may be included in addition to some or all of the first set of instructions.

The invention may also extend to the manufacture of a medical device including the component by combining the component with at least one or more further components.

The communication module may be integrated with a drive mechanism in a drive module for an autoinjector. When installed in an autoinjector the drive module may be configured so that a trigger element of the drive mechanism is held in a retracted position when a cap is attached to a front end of the device prior to use. The trigger element may be coupled directly, or indirectly to a needle guard element which is held in a retracted position by the cap.

In other examples, the communication module may be integrated in a housing module for an autoinjector with a medicament container. The medicament container may be, for example a syringe or cartridge. The medicament container may comprise a movable stopper, movement of which may force a medicament from an outlet. The outlet may comprise a needle to pierce the skin of a user.

With the communication module positioned with the drive mechanism, when the drive mechanism is held in a retracted position by a cap the trigger mechanism may be positioned between a first and second switches of the communication module. When the cap is removed from the autoinjector the needle guard may be biased to a protective position in which it extends further out of a front of the housing than in the retracted position thereby preventing accidental access to a needle of the syringe. The movement of needle guard out of the housing causes, or allows, the trigger element to move towards the front of the housing to a forward position. A first contact switch of the communication module may be arranged to contact a portion of the trigger element, for example a first contact portion of the trigger element, when the trigger element is in the forward position. The first contact portion of the trigger element may be a radially raised portion of the trigger element. This is one example of an arrangement in which the communication module is able to detect removal of a cap of an autoinjector.

To use the autoinjector the needle guard can be pressed onto an injection site and forced backwards into the housing which moves the trigger element backwards away from the forward position. The rearward motion of the needle guard may allow a needle of the syringe to pierce the skin.

When the trigger element reaches a rearmost position, possibly having passed through the retracted position, a plunger of the drive mechanism is released to drive a stopper of the syringe to deliver a medicament (e.g., in the form of a fluid product) to the patient through the needle. A second contact switch of the communication module may be arranged to contact a portion of the trigger element, for example a second contact portion of the trigger element, when the trigger element is in the rearmost position. The second contact portion of the trigger element may be a radially raised portion of the trigger element and may be the same as the first contact portion or may be a different contacting portion of the same radially raised portion of the trigger element.

During injection, the trigger element may be held in place and remain in substantially the same position within the housing relative to the communication module. A delivery indicator element may be included to indicate a state of operation of the drive mechanism. The delivery indicator element may be a completion indicator element to indicate that delivery of a dose is substantially complete. The delivery indicator element may be a triggered indicator element to indicate that the drive mechanism has been activated or triggered.

When dose delivery reaches a predetermined percentage of completion, for example greater than 90% complete, greater than 95% complete, greater than 99% complete, or substantially complete, a delivery indicator element is released and caused to move from an initial position to an indication position. The communication module may include a third contact switch which is arranged to contact a portion of the delivery indicator element, for example an indicator contact portion of the delivery indicator element, when the delivery indicator element is in one of the initial position, or the indication position. The indicator contact portion of the delivery indicator element may be a radially raised portion of the delivery indicator element.

After the delivery of the dose is complete the trigger element may be released. As the autoinjector is removed from the injection site the needle guard can be caused to move forwards out of the housing to prevent accidental access to the used needle. As the needle guard moves forward the trigger element may move forward with the needle guard to the forward position and the contact a portion of the trigger element, for example a first contact portion of the trigger element, may make contact with the first switch of the communication module.

Each contact switch of the communication module, for example the first, second and third contact switches mentioned above, may include a switch contact element. The switch contact element is the part of the contact switch that makes contact with the actuating element of the drive mechanism, for example the contact portion of the trigger element or delivery indicator element. Movement of the switch contact element relative to the switch body, for example, towards or away from a switch body of the contact switch may cause actuation of the contact switch. The switch contact element may be a button which slides into the switch body, or a lever which is pivotable relative to the switch body, or any other suitable element. The contact element may directly actuate the switch, or may cause movement of one or more additional elements that cause actuation of the switch.

An actuating element of the drive mechanism may move along a first axis and a contact switch of the communication module may be arranged so that a contact surface of the switch contact element is arranged to initially extend transverse to the first axis so as to be in the form of a movable ramp, or may be arranged to pivot to form such a ramp.

When the contact switch is not actuated the ramp may have an increasing height in the anticipated direction of travel of the actuating element that is to cause actuation of the contact switch and, when actuated the movable ramp may have moved into, or flattened against the body of the contact switch. In this configuration the initial contact between the actuating element and the switch contact element can be with the lowest height of the ramp and, as the actuating element continues to move along the axis and a contact point between the switch contact element and actuating element moves along the ramp, the switch contact element can move to reduce the ramp height, or flatten the ramp. The use of such a ramp allows control over the forces required to actuate the contact switch.

The ramp may have an angle of between 10° and 20° to the longitudinal axis, for example the ramp angle may be about 15° to the longitudinal axis.

The communication module may include two contact switches which are configured to contact the trigger element. A first contact switch may be configured to contact the trigger element in a forward position, and a second contact switch may be configured to contact the trigger element in a rearmost position. Each contact switch may include a switch contact element, and the switches may be arranged such that movable ramps formed by the contact surfaces of the switch contact elements are directed towards one another, with the lowest height of the ramps being closest to one another along the first axis.

To construct an autoinjector, a drive module, which contains the drive mechanism and the communication module, may be inserted into an elongate hollow housing which contains a needle guard assembly and a syringe containing a medicament.

Certain autoinjector embodiments described herein, as provided to an end user, will generally include a fluid product containing an active pharmaceutical ingredient (API). In some cases, the API is formulated for subcutaneous delivery. Alternatively, the API can be formulated for intradermal delivery. As yet another alternative, the API can be formulated for intramuscular delivery. The autoinjector can be configured to (e.g., subcutaneously) deliver from 0.1 to 5 mL of fluid product, preferably from 0.25 to 2 mL fluid product, more preferably from 1 to 2 mL fluid product, or about 0.25 mL, 0.5 mL, 1 mL, 1.5 mL, or 2 mL of fluid product. In some embodiments, the autoinjector therefore can comprise or contain from 0.1 to 5 mL of fluid product, preferably from 0.25 to 2 mL fluid product, more preferably from 1 to 2 mL fluid product, or about 0.25 mL, 0.5 mL, 1 mL, 1.5 mL, or 2 mL of fluid product, wherein said fluid product is configured for delivery to a subject. As used herein, an autoinjector comprising or containing a volume of fluid product configured for delivery can additionally comprise an overfill to ensure delivery of an entire specified volume configured for delivery to the subject. In some embodiments, the API in an autoinjector described herein can be formulated at a high concentration, e.g., for subcutaneous or intramuscular delivery. For example, the API can be formulated at a concentration of from about 10 mg/mL to about 300 mg/mL, from about 25 mg/mL to about 250 mg/mL, from about 50 mg/mL to about 175 mg/mL, from about 75 mg/mL to about 175 mg/mL, from about 75 mg/mL to about 150 mg/mL, or about 25, 50, 100, 125, 150, or 175 mg/mL. In some embodiments, the API is or comprises a peptide or protein sequence. For example, the API can be or comprise a peptide ligand, a protein enzyme, or an antibody or antigen-binding fragment thereof. In some embodiments, the API is or comprises a bispecific antibody, or a bispecific antigen-binding fragment thereof. In some embodiments, the API is or comprises an Fc region of an antibody, or a derivative thereof. In some embodiments, the API comprises a sequence of amino acids (e.g., a peptide, a protein, an Fc region of an antibody, an antibody or an antigen binding fragment thereof), a linker, and a toxin or radionuclide. In some embodiments, the API is or comprises a cytokine, a hormone, or an interferon (e.g., interferon beta-1b, or interferon alpha-2b). In some embodiments, the API is a drug suitable for chronic pain relief, or palliative care, such as an opioid. In some embodiments, the API is an IL-17 antagonist, such as an antibody that binds IL-17, a dimer comprising IL-17A, and/or a dimer comprising IL-17A and IL-17F. In some embodiments, the API is bimekizumab, ixekizumab, or secukinumab. Exemplary APIs suitable for an autoinjector described herein, include but are not limited to adalimumab, abatacept, alemtuzumab, basiliximab, canakinumab, crizanlizumab, daratumumab, darbepoietin, emecizumab, erenumab, etanercept, factor Vila, fentanyl, infliximab, iscalimab, lenacapavir, morphine, natalizumab, ofatumumab, omalizumab, rilonacept, rituximab, and trastuzumab.

The invention will now be described by way of example only with reference to the following figures in which.

It is to be understood that the different features and elements illustrated described in the following examples are not inextricably linked to each other and may, alternatively, be provided without the presence of others of the features. It is also understood that the Figures and references to the Figures described in the following examples are not intended to limit the scope of the inventions described herein.

Figures 1A, 1B:
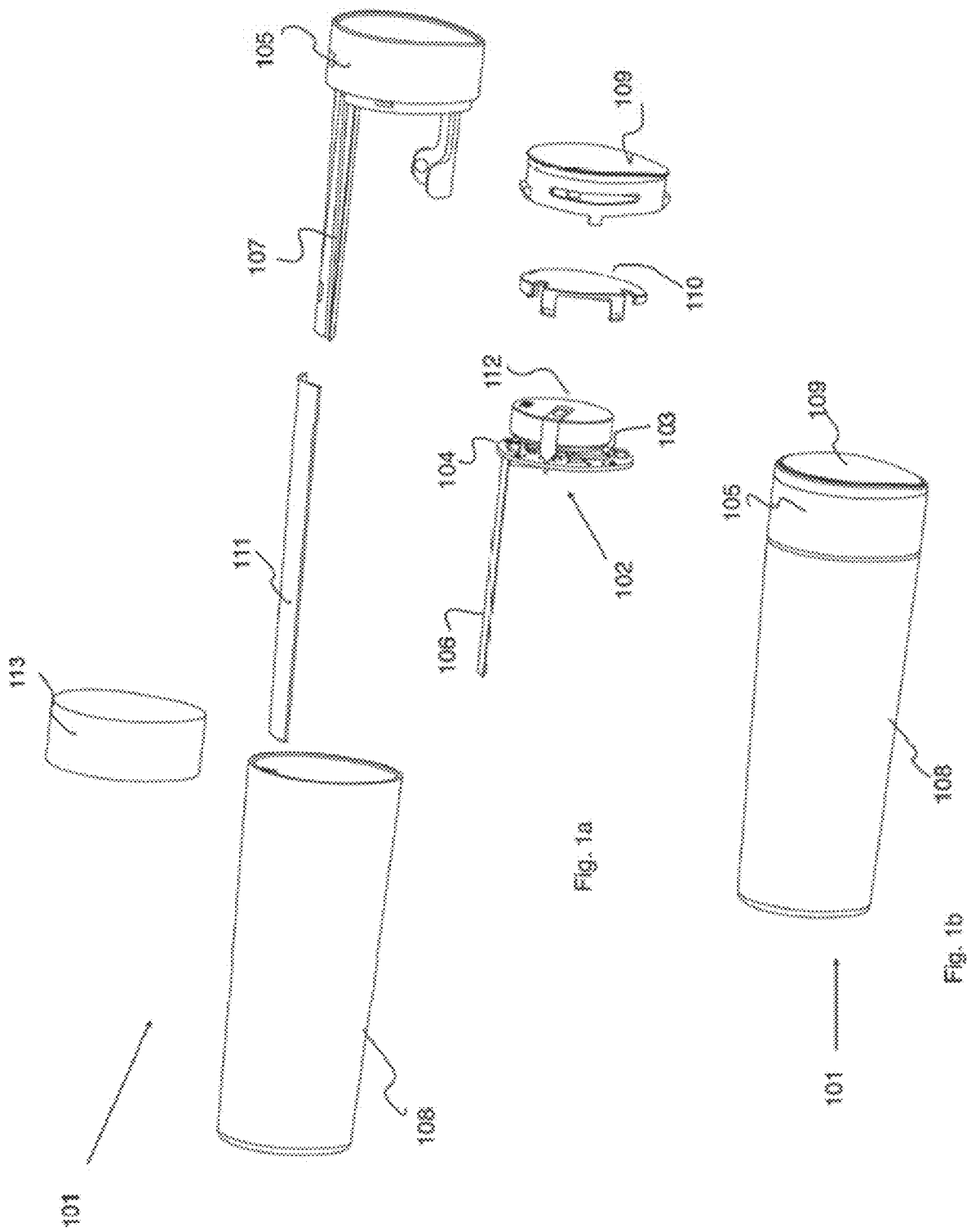
FIGS. 1a, 1b illustrate a reusable communication element.

FIGS. 1a and 1b illustrate an example of a reusable communication element 101 which may be mounted on existing autoinjectors. FIG. 1a is an exploded view, FIG. 1b shows the reusable communication element in assembled form.

The communication element 101 of this example comprises a communication module 102 with a main board, in this case a printed circuit board 103 onto which a processor, in this case a microcontroller, and detectors, in this case an accelerometer and a microphone are mounted.

The printed circuit board 103 may be attached to a support 104 with which it is inserted into a housing 105. Furthermore, an NFC antenna 106 may be provided, being coupled to the printed circuit board 103.

In this example, the housing comprises a snap-fit element 107. A sleeve 108 is provided which partly accommodates the housing 105 with the communication module. In particular, the housing is partly inserted into the sleeve so that, inter alia, the snap-fit element is completely contained within the sleeve. The sleeve has a hollow construction so that it can be slipped onto an autoinjector. The housing into which the communication module has been inserted is enclosed with a cap 109 together with a cap insert 110. Other connection mechanisms may be used in other examples.

Between the cap insert 110 and the printed circuit board 103, a battery 112 may be arranged which can serve as power supply for the communication module 102.

The sleeve 108 and/or the housing 105 may be made of a transparent material.

Additionally, a label 113 may be provided to enclose the cap 109 within the housing 105. In case of a transparent housing 105, the cap insert 110 and any markings thereon may be visible from the outside. The snap-fit element 107 may be hidden beneath a cover element 111.

The printed circuit board 103 together with the accelerometer and the microphone may be part of a detector component to detect an injector usage event. For example, as different elements of the autoinjector, such as the syringe or a completion indicator element will generate noises and small shocks when being moved during operation, both the microphone and the accelerometer measure signals which allow for a detection of corresponding injector usage events.

These detector elements may enable detection of removal of the cap of the autoinjector and/or removal of the autoinjector from the injection site such as a patient's skin area.

The communication module, furthermore, comprises a transmitter component which is, in this example, a BLE module being mounted to the printed circuit board 103 as well. Such a BLE module enables fast and efficient pairing of the communication module with a users smartphone, or other suitable receiving device such as personal computer, laptop, tablet or smart hub, so as to transmit data in an efficient way.

The transmission of obtained or acquired injector usage information may be done in different alternative ways. According to a first option, each time a specific event is detected, e.g. start of an injection process or completion of injection process, the transmitter component directly transmits wirelessly the respective injector usage information to the receiving device, such as a users smartphone. In this case, a timing device, for example a clock, is not necessarily required on the side of the communication module as correlating the detected events with a certain time may be performed on the side of the receiving device, such as a smartphone.

Alternatively, the communication module may save a plurality of detected events, for example all detected events starting with the removal of the cap until removal of the autoinjector from the injection site, and stores the data together with time information. For this purpose, the communication module, particularly the detector component, can comprise a memory in which the data is stored. The memory may be volatile or non-volatile memory.

According to a further alternative, transmission of the injector usage information may be performed even at a later stage after having detected, recorded and stored a plurality of injection processes.

Upon receipt of a trigger signal, the stored injector usage information may be transmitted to the receiving device. The trigger signal may be received from the receiving device, e.g. the smartphone. For example, a user may click on a "Synchronize" button in a respective application on the smartphone. Alternatively, the trigger signal may be issued by the detector component upon detection of a predetermined event such as completion of the injection process.

The autoinjector may be configured as described, for example, in WO 2019/224783, the content of which is incorporated herein by reference.

Figure 2:
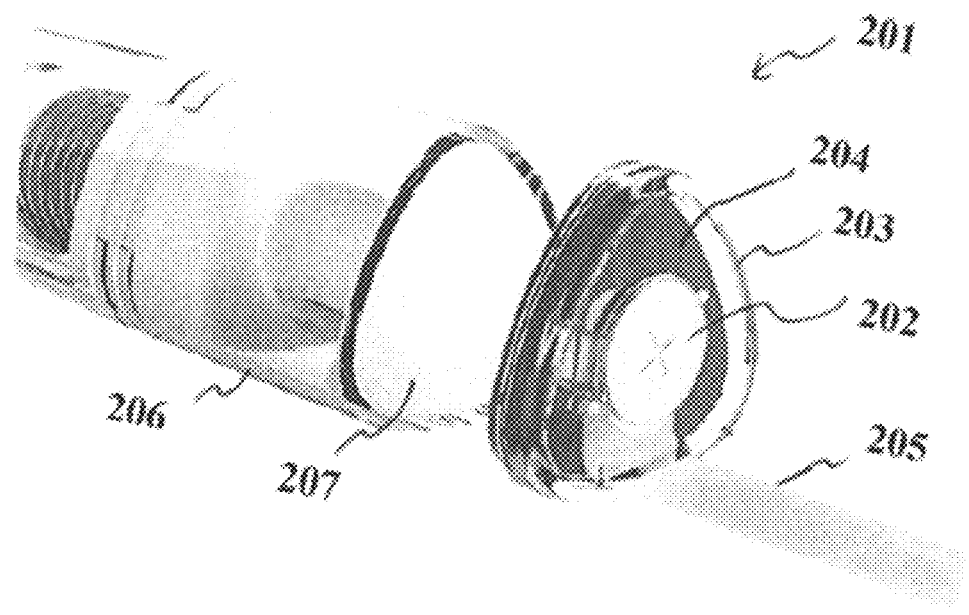
FIG. 2 illustrates another communication element.

An alternative reusable communication element 201 for an autoinjector is illustrated in FIG. 2. This reusable communication element 201 of this example comprises a battery 202 for powering the communication module. The communication element has a housing 203. Within the housing 203, a printed circuit board 204 is provided. In the example as illustrated, the housing 203 is transparent; it is to be understood, however, that this need not be the case for some, or all, of the housing.

In some examples a sheet or strip of an insulating material 205 may be arranged between the battery 202 and one or more of its electrical contacts on the printed circuit board 204. The sheet may be removed when the autoinjector is put into operation. As an example, the part of the sheet projecting out of the housing of the communication element may be fixed to a part of the package in which the autoinjector together with the communication element is stored. Upon removal of the autoinjector, the sheet remains fixed to the package and, thus, will be pulled out so as to enable an electrical contact between the battery and the electrical contacts on the PCB.

Generation of an electrical contact may also activate the communication module.

The reusable communication element 201 may be bonded onto an autoinjector. For this purpose, the communication element 201 may be provided with an adhesive layer or coating covered by a protective film. In an example, the top surface of the autoinjector 206 has a mounting pad 207 which may be made of some epoxy, plastic or other material. When mounting the communication onto the autoinjector, the protective film may be removed.

Figure 3B:
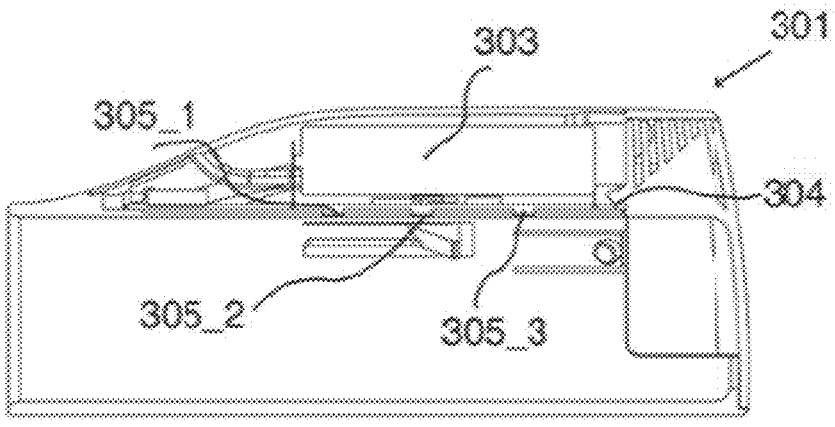
FIGS. 3a, 3b show another reusable communication element.
Figure 3A:
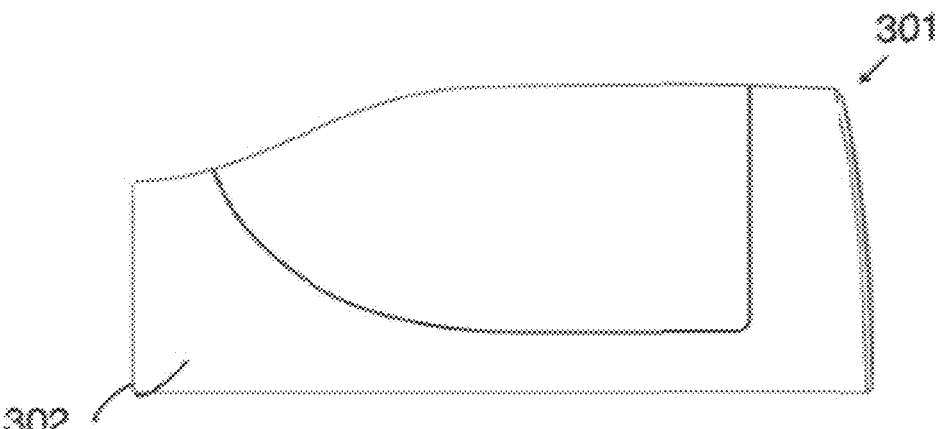

FIG. 3*a* shows an exterior view of a reusable communication element 301 with a sleeve 302 to be slid onto an autoinjector. FIG. 3*b* is a sectional view of this reusable communication element.

The reusable communication element 301 of this example comprises a battery 303 as a power source so that it may be reusable with a plurality of autoinjectors. The battery 303 is electrically connected to a printed circuit board 304. To the printed circuit board 304, Hall effect sensors 305_1, 305_2 and 305_3 are mounted which are to be used as switches. These Hall effect sensors form part of the detector component. In other examples, different sensors or a different arrangement of sensors may be used.

Figure 4A:
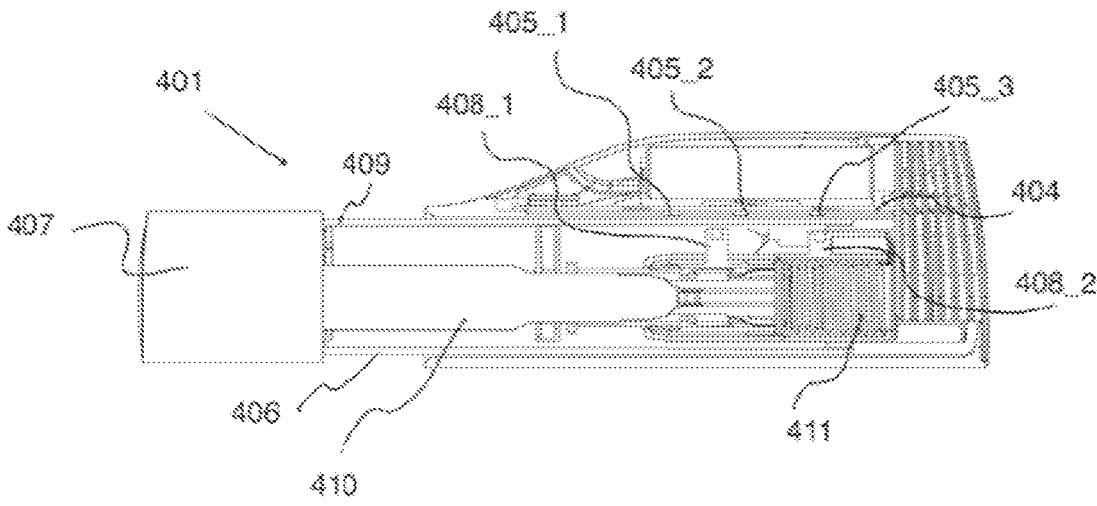
FIGS. 4a to 4e show sectional views of a reusable communication element mounted to an autoinjector.

FIG. 4*a* illustrates a configuration in which a reusable communication element, here denoted as 401, as shown in FIGS. 3*a* and 3*b* is mounted on an autoinjector 406. The configuration shows the autoinjector with mounted cap 407. The communication element of this example comprises three non-contact switches in the form of Hall effect switches including Hall effect sensors 405_1, 405_2 and 405_3 as well as two switching elements 408_1 and 408_2 each comprising a magnet. In this example the first switching element 408_1 is part of a trigger element of a drive mechanism of the autoinjector 406. The second switching element 408_2 is part of a dose complete indicator of a drive mechanism of the autoinjector 406.

In the configuration according to the example of FIG. 4a, the left/first switching element 408_1 is situated between the leftmost/first Hall effect sensor 405_1 and the middle/second Hall effect sensor 405_2. Thus, neither the first Hall effect switch, nor the second Hall effect switch are "switched on", i.e. activated.

However, the right/second switching element 408_1 is situated directly below the rightmost/third Hall effect sensor (i.e. in close proximity). Thus, the third Hall effect switch is switched on or activated.

As also described in more detail in WO 2019/224783, in the assembled or initial state of the autoinjector 406 with reusable communication element 401 (FIG. 4a), the end cap 407 is screwed onto, or otherwise secured to, the longitudinal housing 409, wherein the end cap 407 is held in circumferential direction by an engagement of inner protrusions formed on the proximal end of the housing within a corresponding receiving space between two projections and formed inside the end cap body. Thereby, the re-movable cap 407 is held on the housing against an axial withdrawing force by the projections as well as against small twist-off forces, which are below a twist-off force threshold value, by opposing projections forming a receiving space.

In this state, the first and second switch are both deactivated while the third switch is activated. This combined switch statuses (which may be parametrized as "001") corresponds to the injector usage event "cap-on". This event or its detection may be stored in a memory of the communication element which may be mounted on the printed circuit board. Moreover, in the assembled state, a syringe is held within a syringe holder.

From this fully assembled initial position, the device can be used as follows:

Under rotation between the removable end cap 407 and the housing 409 performed by a user by applying a twist-off force, the safety shield 410 is pressed out by the safety shield spring 411 in proximal axial direction.

Figure 4B:
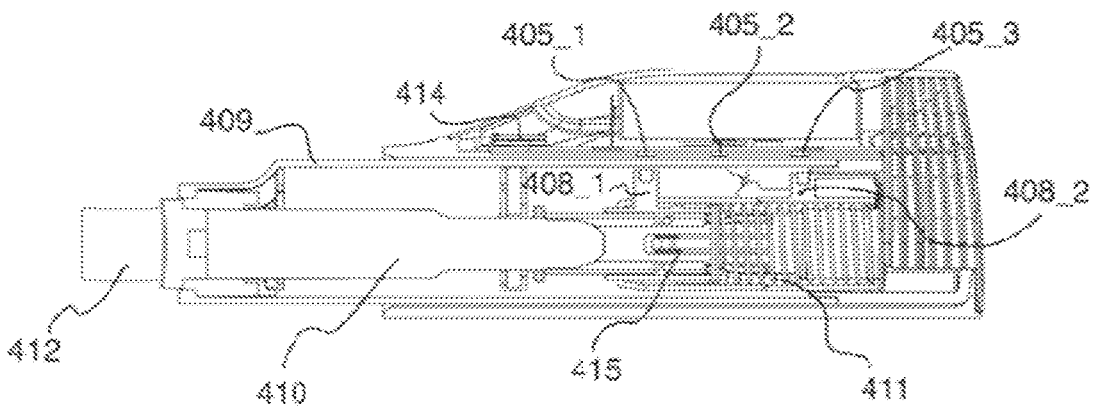

FIG. 4b shows a view in a condition in which the removable cap is entirely removed from the longitudinal housing 409 and the device is ready for dispensing the fluid product. One can see that the removable end cap is fully separated from the housing 409. The proximal portion 412 of the safety shield 410 fully projects out of the housing 409 and covers the injection needle with its needle tip.

Removal of the cap leads to displacement of the first switching element 408_1 towards the first Hall effect sensor 405_1. This leads to activation or switching on of this first sensor/switch of the detector component and this may lead to the activation, or powering on, of other components of the communication module; the relative position of the second switching element 408_2 and the third Hall effect sensor 405_3 remains unchanged. The combined switch statuses (which may be parametrized as "101") now correspond to the injector usage event "Cap removal". Detection of this event may be stored in the memory of the communication element.

Detection of the cap removal event may also activate the transmitter component 414 which is also mounted to the printed circuit board 404.

Figure 4C:
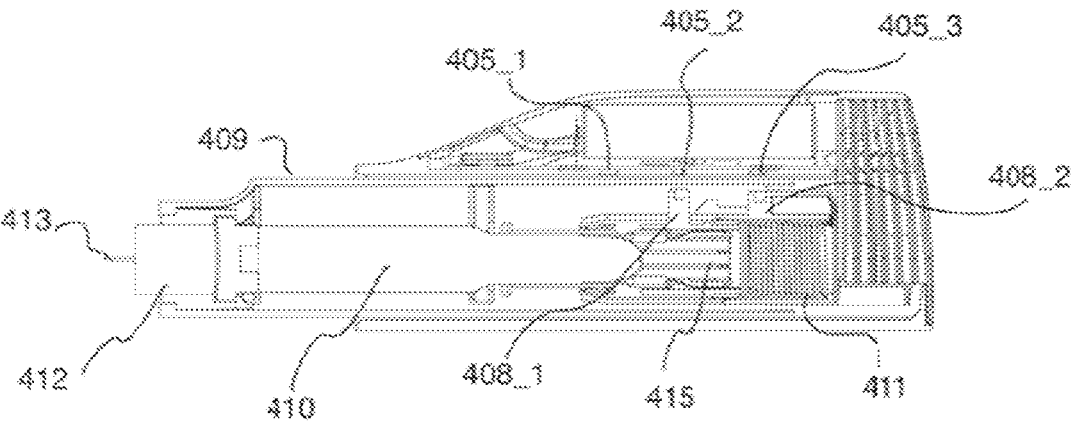

By further pressing the autoinjector against the patient's skin, the safety shield 410 can be moved in distal direction into the housing 409, whereby the needle 413 is pierced into the patient's skin and the situation as shown in FIG. 4c is reached. In a condition in which the device is pressed against a patient's skin, the injection needle is pierced into the patient's skin, the safety shield 410 is fully de-pressed into the longitudinal housing 409 and dispensing of the fluid product is initiated.

In the example shown in FIG. 4c, depressing the safety shield 410 is fully into the longitudinal housing 409 leads to displacement of the first switching element 408_1 towards the second Hall effect sensor 405_2. This results in activation or switching on of this second sensor/switch of the detector component; the relative position of the second switching element 408_2 with respect to the third Hall effect sensor 405_3 remains unchanged. The combined switch statuses (which may be parametrized as "011") now correspond to the injector usage event "Start of dispensing fluid product". Detection of this event may be stored in the memory of the communication element.

Due to the relative movement between the safety shield 410 and the housing 409, the needle 413 is exposed and protrudes into the patient's skin. Under the action of a main spring (not shown), the plunger 415 is pressed in axial direction. Thereby, the drug is pressed out of a glass body of the syringe through the injection needle 413 into the patient's tissue.

This process continues for a full dispensing of the drug into the patient's tissue.

Figure 4D:
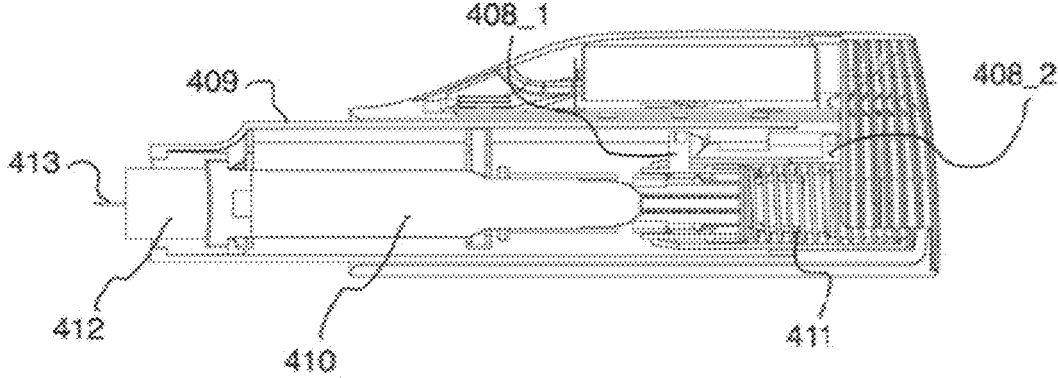

FIG. 4d show a view in a condition in which the fluid product is being nearly entirely dispensed. In this stage of the device, the right/second switching element 408_2 is free to move in distal direction so that the second switching element 408_2 moves away from the third Hall effect sensor 405_3 in distal direction which is, thus, deactivated.

In this position, the second switch remains switched on. This combined switch statuses (which may be parametrized as "010") correspond to the injection usage event "End of dispensing fluid product").

When the dose has been fully dispensed into the patient's tissue, the autoinjector 406 with the reusable communication element 401 can be removed from the injection site.

Figure 4E:
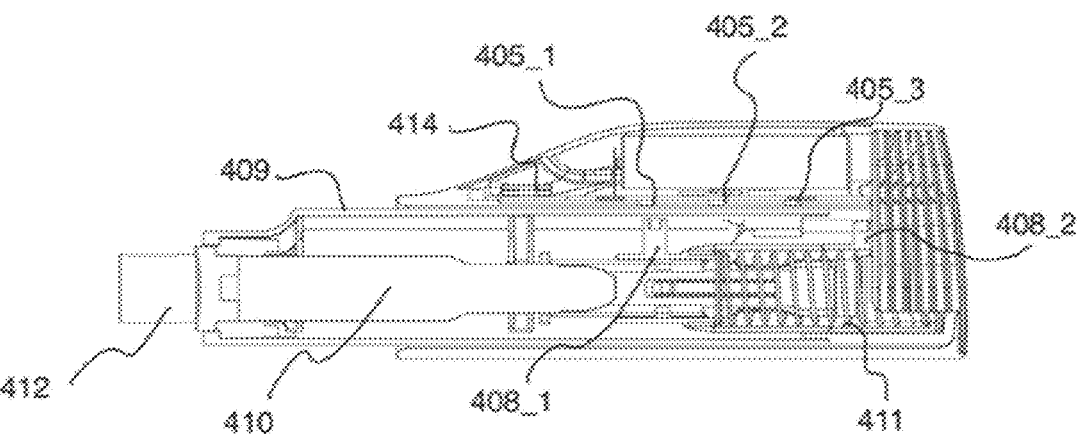

In the situation illustrated in FIG. 4e, the housing 409 has been lifted so far from the patient's skin, that the needle is fully covered by the proximal end portion 412 of the safety shield 410 and the proximal end portion 412 extends beyond the sharpened needle tip of the injection needle. In other words, due to the action of the expanding spring 411, the safety shield 410 is pressed to such an extent out of the housing 409, that it fully covers the needle and protrudes over the needle tip.

In this case, the second and third switches are deactivated while the first switch is activated. This combined switch statuses (which may be parametrized as "100") correspond to the injection usage event "Removal from injection site").

Recording of the "removal from injection site" event triggers transmission of the injector usage information to the receiving device via the transmitter component 414.

Figure 5:
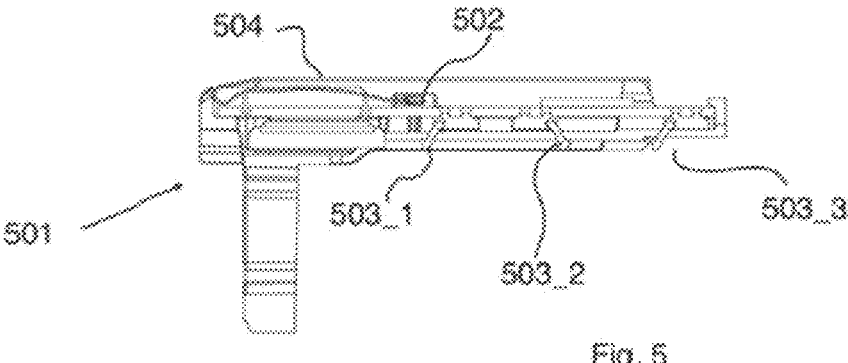
FIG. 5 shows a sectional view of a communication module.
Figure 6:
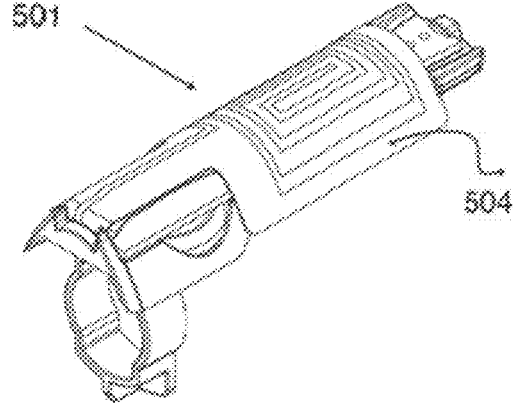
FIG. 6 shows a an upper side view of the communication module of FIG. 5.

A communication module for integration within an autoinjector is illustrated in the sectional view of FIG. 5 and the upper side view of FIG. 6. In this configuration, the detector component comprises contact switches to detect the different events or steps of the injection process.

The communication module 501 of this example comprises a printed circuit board (PCB) 502 with a microcontroller. As shown in FIG. 5, below, on the opposite side of the PCB, three contact switches 503_1, 503_2 and 503_3 are arranged, forming part of the detector component. In the state of FIG. 5, all three switches 503_1, 503_2 and 503_3 are deactivated, i.e. no electrical contact is established. This state may be parametrized as "000".

FIGS. 5 and 6 also show an additional NFC element 504. The NFC element 504 is optional; other transmitter components may be provided as well or instead. FIGS. 7*a* to 7*e* illustrate a sequence of injection process steps for an example autoinjector 701 with integrated communication module, analogously to the case of FIGS. 4*a* to 4*e*. The integrated communication module is similar to the one shown in FIGS. 5 and 6, but does not comprise an NFC element. Instead, a BLE transmitter component is employed, but other transmitter components may be used. In other examples, fewer, or additional usage steps may be recorded.

Figure 7A:
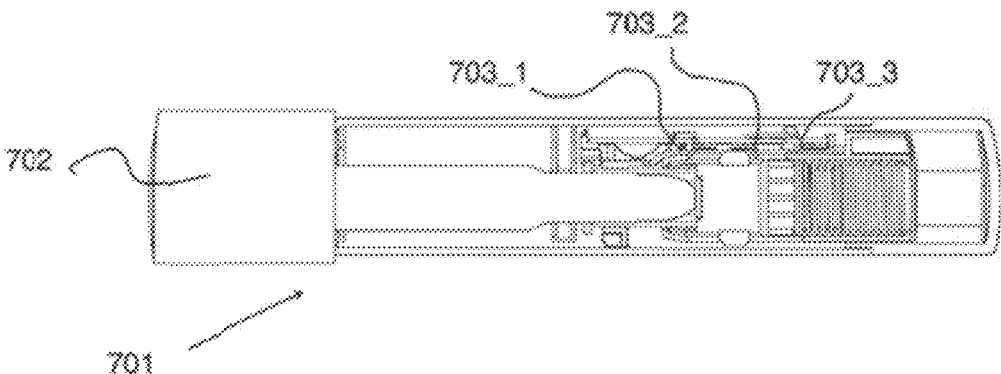
FIGS. 7a to 7e show sectional views of an autoinjector with integrated communication module.

In FIG. 7*a*, the autoinjector 701 is in its initial configuration with a cap 702 still present. Three contact switches 703_1, 703_2 and 703_3 are provided that are switched on/activated by pushing them upwards so that an electrical contact is established.

In this state, the first and second switch 703_1, 703_2 are both not activated while the third switch is activated/switched on as it is pushed upwards. This combined switch statuses (which may be parametrized as "001") correspond to the injector usage event "Cap-on".

Figure 7B:
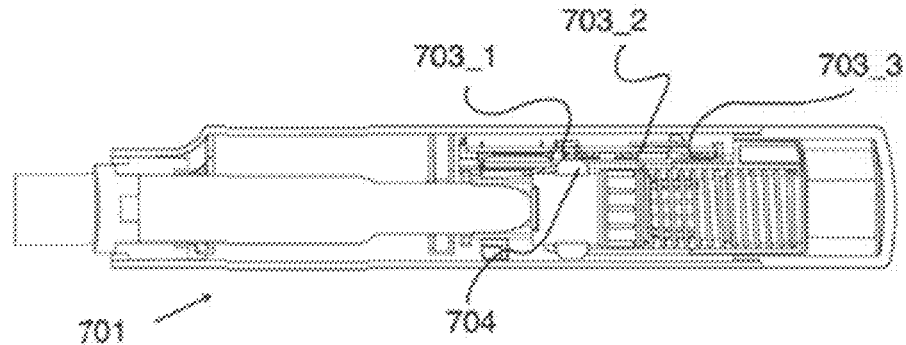

In FIG. 7*b*, the cap has been removed. The removal of the cap leads to a movement of switching trigger 704 to the left so that the first switch 703_1 is pushed upwards and, thus, activated/switched on. The second switch 703_1 remains deactivated, the third switch 703_3 remains activated. This combined switch statuses may be parametrized as "101" and correspond to the event "Cap off".

The operation of the first switch 703_1 activates the system including (the active parts of) the detector component and the transmitter component by establishing electrical contact between the battery and the printed circuit board, or otherwise enabling one or more components. The detection of this event is recorded.

Placing the autoinjector onto the injection site and pressing it against the patient's skin will operate the second (middle) switch 703_2 while deactivating the first switch 703_1. The combined switch statuses may be parametrized as "011". The detection of this event is recorded as "Start of the injection process".

Figure 7C:
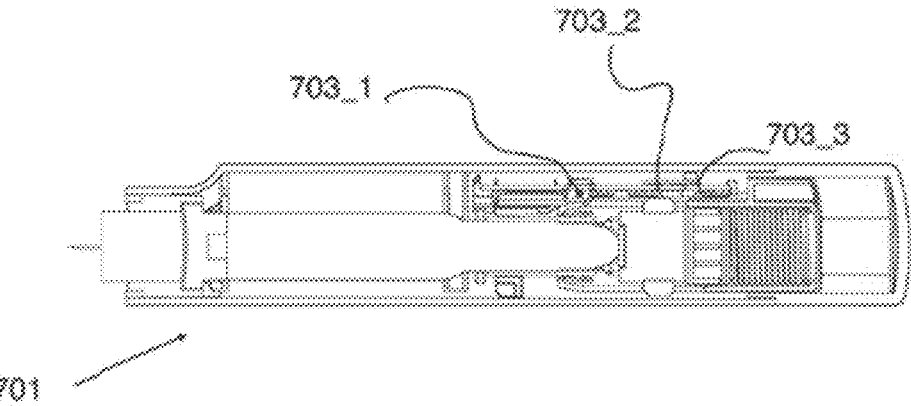

FIG. 7*c* illustrates the situation in which the injection needle is pierced into the patient's skin and dispensing of the fluid product is initiated. The depth of piercing may be pre-set, or may be adjustable, to be appropriate for the medicament being delivered, for example for a subcutaneous, intramuscular or intradermal injection.

Figure 7D:
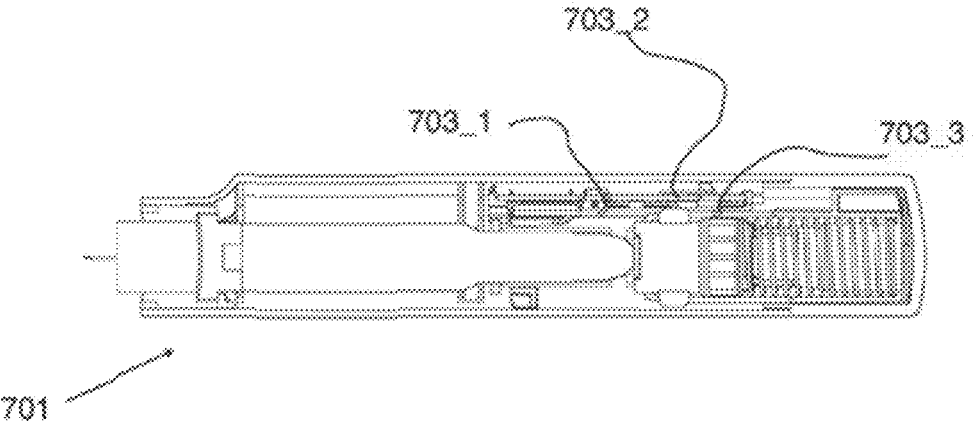

FIG. 7*d* shows a view in a condition in which the fluid product is being nearly entirely dispensed. The first switch 703_1 and the third switch 703_3 are deactivated, whereas the second switch 703_2 is activated. This combined switch statuses (which may be parametrized as "010") correspond to the injection usage event "End of dispensing fluid product").

Figure 7E:
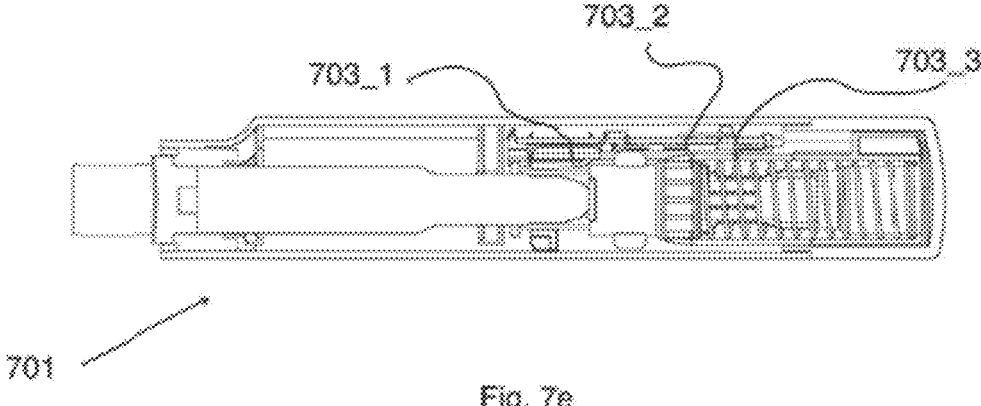

In the situation illustrated in FIG. 7*e*, the housing has been lifted from the patient's skin, so that the needle is fully covered by the proximal end portion of the safety shield and the proximal end portion extends beyond the sharpened needle tip of the injection needle.

In this configuration, the first switch 703_3 of the example autoinjector is operated indicating the completion of the injection process. Thus, the second and third switches 703_2 and 703_3 are deactivated while the first switch 703_1 is activated. This combined switch statuses (which may be parametrized as "100") correspond to the injection usage event "Removal from injection site").

This event is recorded in memory. A trigger signal may be issued triggering the transmitter component to build up, or establish, communication with a receiving device, e.g. a user's smartphone, via Bluetooth, or other wireless communication, and transmit the recorded data about the injection process from the communication module to the receiving device. Alternatively, if the receiving device is within reach, the injector usage information may be transmitted continuously to the receiving device during the complete operation/ at least some of the period of use of the autoinjector.

Figure 8:
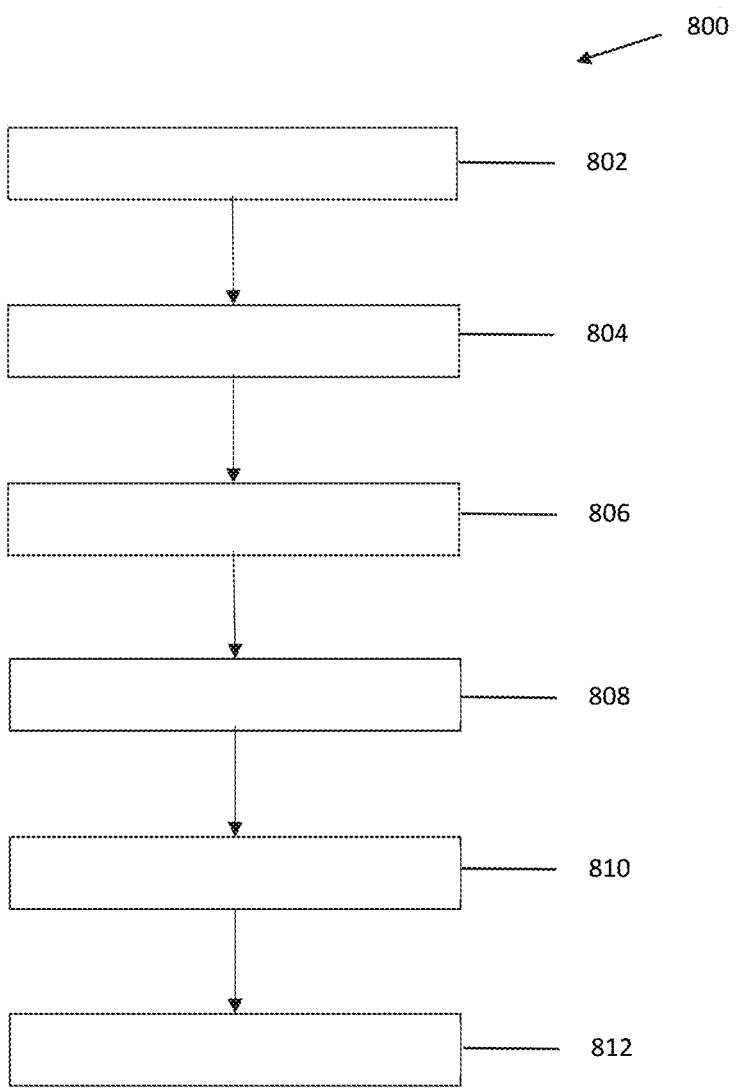
FIG. 8 shows a flow chart for assembling an autoinjector.

FIG. 8 shows a flowchart of a method 800 of manufacturing a medical device. In this case the medical device is an autoinjector, but could be any other medical device, for example a medicament delivery device or monitoring device. The medical device may be disposable or reusable. The medical device comprises a communications module, and the method comprises the following:

Assembling 802 a preliminary assembly. The preliminary assembly may be any suitable assembly for constructing a medical device, for example a drive module for an autoinjector, a housing module for an autoinjector or other medical device, or other sub-assembly.

In this example the preliminary assembly comprises a communications module comprising a main board, power source, processor, a detector component configured to detect a usage event to obtain usage information, and a transmitter component configured to wirelessly transmit usage information to a receiving device. The power source, processor, detector component and transmitter may be attached to the main board. The main board comprises at least one component having a memory which includes a first set of instructions.

After assembling 802 the preliminary assembly, the processor is used 804 to interpret the first set of instructions. In this example the first set of instructions cause the processor to put the communication module into a test mode for a test period and then, after expiry of the test period, into a pre-assembly mode. In the test mode the detector component and the transmitter component are enabled, for example using software, or by power being provided from the power source to the detector component and the transmitter component, to allow preliminary testing of the component function. In the pre-assembly mode the detector component and the transmitter component are not enabled, for example using software, or by no power being provided to the detector component or the transmitter component, so that power is saved.

In the pre-assembly mode the preliminary component may be stored and/or shipped 806 prior to installation into a sub-assembly or a final device form.

Prior to, or as part of, such installation, the memory of the pre-assembly mode communication module can be altered 808 such that that the instructions therein comprise a second set of instructions. The processor can then be used to interpret the second set of instructions. The second set of instructions may cause the processor to put the communication module into an assembly mode in which the detector component is enabled, for example through software or by receiving power and, upon detection of a usage event, the processor changes the communication module into a use mode in which the detector component and the transmitter component are enabled, for example through software or by power being provided from the power source to the detector component and the transmitter component.

The altering 808 of the memory to contain the second set of instructions may occur prior to, or during, the installation of the preliminary assembly into a sub-assembly or a final device form.

The method may comprise installing 810 the preliminary assembly into a sub-assembly or final device form of a medical device. In this example, the sub assembly is a drive module of an autoinjector, but in other examples could be a housing module, or other sub assembly. The drive module may comprise a drive mechanism including a trigger element for controlling an operation of the drive mechanism, and installing the preliminary assembly comprises aligning the detector component to allow the detector component to detect a position of the trigger element. The sub-assembly may be a drive module of an autoinjector. The drive module may comprise a drive mechanism including an indicator element for indication a state of operation of the drive mechanism and installing the preliminary assembly comprises aligning the detector component to allow the detector component to detect a position of the indicator element. The sub-assembly can then be installed into a final device for use 812.

It is to be understood that the above embodiments are only exemplary and the disclosed features may be provided in other combinations. For example, the different types of switches disclosed in the different embodiments (e.g. contact and non-contact switches) may be combined in other ways. Furthermore, the number, arrangement and activation/deactivation of the different switches depending on the injector usage events may vary as well.

A skilled person will appreciate that, where Hall effect sensors are described in the foregoing and following embodiments, other suitable non-contact sensors, such as magnetoresistive (AMR/GMR/TMR) sensors, may also be used in the same or a similar configuration.

FIGS. 9a to 9g show sectional views of an example of an autoinjector drive module 900. The drive module 900 comprises a communications module 902 and a drive mechanism 904. The drive mechanism 904 of this example comprises a trigger element 906, an indicator element 908 and a plunger rod 910. The communications module 902 comprises a detector component which, in this example, comprises a first contact switch 912, a second contact switch 914 and a third contact switch 916. The communications module 902 also comprises a transmitter component 918. The first contact switch 912, second contact switch 914 and third contact switch 916 are distributed along a first axis 920. Each of the first contact switch 912, second contact switch 914 and third contact switch 916 include a switch contact element 930 extending from a switch body 932 transverse to the first axis 920. The switch contact elements 930 provide a contact surface which will make contact with an actuating element and are attached at an end to the switch body so that the switch contact elements 930 can pivot when a force is applied through contact with an actuating element. The contact surface of the switch contact elements 930 may be biased to extend at an angle of between 10° and 20° to the longitudinal axis, for example the ramp angle may be about 15°. In this example the contact elements 930 of the first and third contact switches 912,916 are pivoted so that a free end can be moved towards a first, injection, end of the drive module 900. In this example the contact element 930 of the second contact switch 914 is pivoted so that a free end can be moved towards a second, opposite, or rear, end of the drive module 900.

Figure 9A:
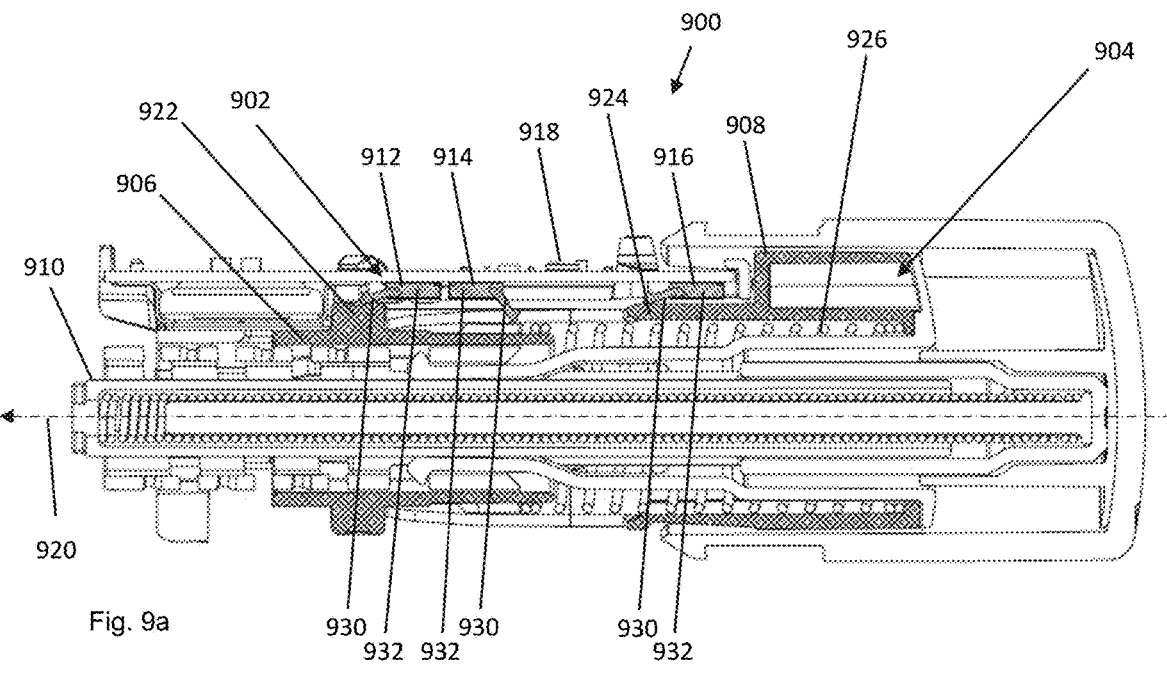
FIGS. 9a to 9g show sectional views of an autoinjector drive module.

FIG. 9a shows the autoinjector drive module 900 of this example in an example of a pre-assembled state. In the pre-assembled state a radial projection, or raised portion, 922 of the trigger element 906 is biased by a trigger spring 926 to a forward position in which it is axially aligned with, and actuates, the first contact switch 912. In the pre-assembled state of this example a portion 924 of the indicator element 908 is axially aligned with, and actuates, the third contact switch 916. As set out above, the communication module 902 in this preassembled state may include a component having a memory comprising a first set of instructions. Following testing the transmitter component and the detector component of the communication module 902 are both disabled to reduce power use and risk of accidental actuation of the detector component.

Figure 9B:
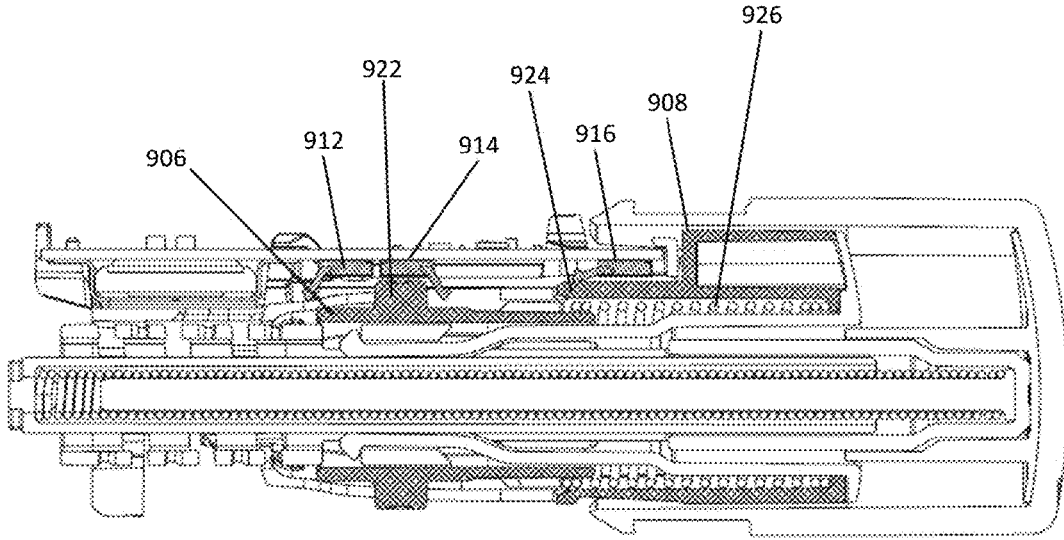

FIG. 9b shows the autoinjector drive module 900 in a cap-on state. In the cap-on state the drive module 900 is installed into an autoinjector (not shown in these figures) and a cap is installed on the autoinjector. As set out above, the communication module 902 in this assembled state may include a component having a memory comprising a second set of instructions. The second set of instructions mean that the communication module is in the assembled state in which at least a portion of the detector element is enabled. In this example it is the first contact switch 912 that is enabled.

The cap installed on the autoinjector causes a needle guard to be held in an intermediate position. The needle guard forces the trigger element 906 to be held against the biasing force of the trigger spring 926 in a retracted position in which the radial projection 922 of the trigger element 906 axially between first contact switch 912 and the second contact switch 914 so neither switch is actuated. In the cap-on state a portion 924 of the indicator element 908 remains axially aligned with, and actuates, the third contact switch 916.

Figure 9C:
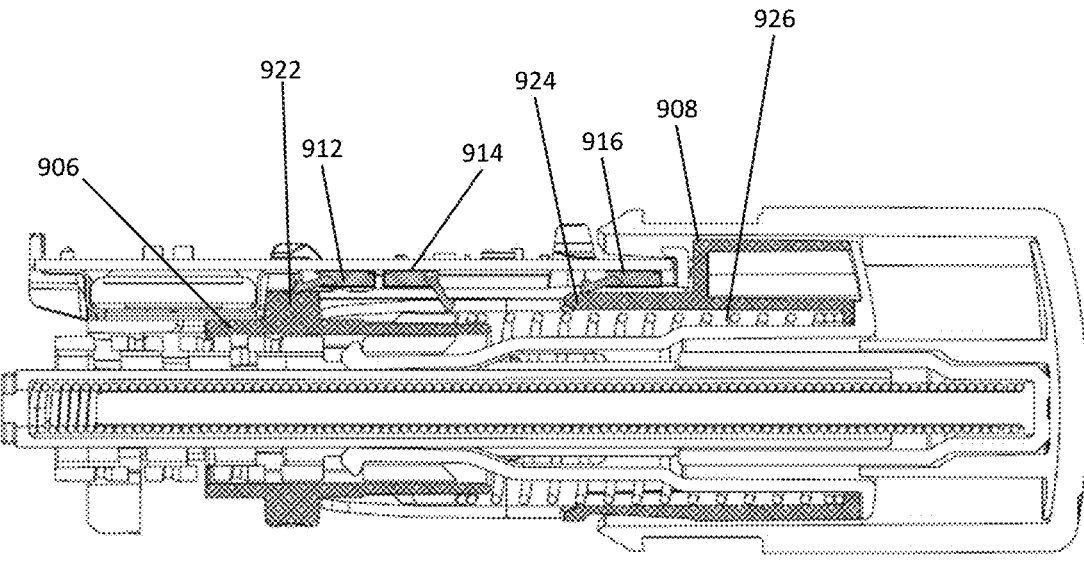

FIG. 9c shows the autoinjector drive module 900 in a cap-off state. In the cap-off-state the drive module 900 is installed into an autoinjector as in FIG. 9b, but the cap has been removed allowing the trigger element 906 to be biased by the trigger spring 926 to the forward position in which the radial projection 922 of the trigger element 906 is axially aligned with, and actuates, the first contact switch 916. This actuation of the first contact switch 912 through cap removal may cause a processor to change the communication module into a use mode, which may trigger activation of one or more additional components the communication module. In the cap-off state a portion 924 of the indicator element 908 remains axially aligned with, and actuates, the third contact switch 916. As set out above, this change of state of the first contact switch 912 may be recorded as an injector usage event.

Figure 9D:
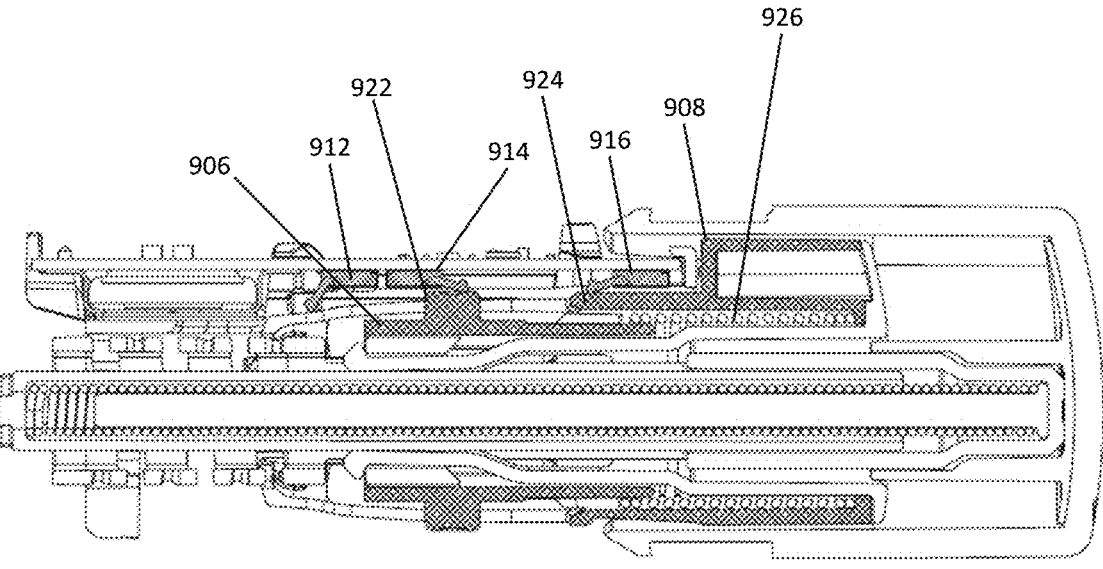

FIG. 9d shows the autoinjector drive module 900 in a triggered state. In the triggered state the drive module 900 is installed into an autoinjector, the cap has been removed as in FIG. 9c and the needle guard of the autoinjector is pressed against the skin of a user to force the needle guard back into a body of the autoinjector. The movement of the needle guard into the autoinjector housing forces the trigger element 906 backwards against the biasing force of the trigger spring 926 into a rearmost position in which the radial projection 922 of the trigger element 906 axially aligned with the second contact switch 914 so that the second contact switch 914 is actuated. In the triggered state a portion 924 of the indicator element 908 remains axially aligned with, and actuates, the third contact switch 916. As set out above, this change of state of the first and second contact switches 912,914 may each be recorded as an injector usage event.

Figure 9E:
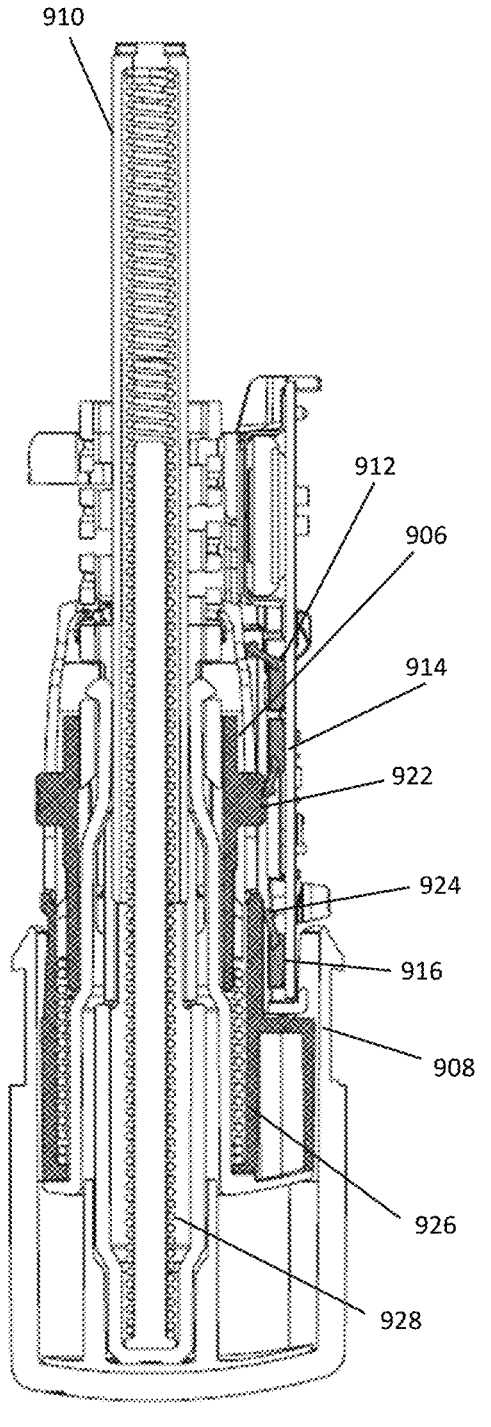

FIG. 9e shows the autoinjector drive module 900 in a delivering state. In the delivering state the drive module 900 is installed into an autoinjector and the needle guard of the autoinjector is pressed against the skin as in FIG. 9d and movement of the trigger element 906 to the rearmost position releases the plunger rod 910 allowing it to be biased forward by a drive spring 928 and act upon a plunger of a syringe in the autoinjector to deliver a dose of medicament. In the delivering state the radial projection 922 of the trigger element 906 remains axially aligned with the second contact switch 914 so that the second contact switch 914 is actuated, and a portion 924 of the indicator element 908 remains axially aligned with, and actuates, the third contact switch 916. In this example, during delivery there may be no change of state of the contact switches, although other detection elements could be used, for example optical sensors, microphones, accelerometers or other sensors. A change of state may be recorded as an injector usage event.

Figure 9F:
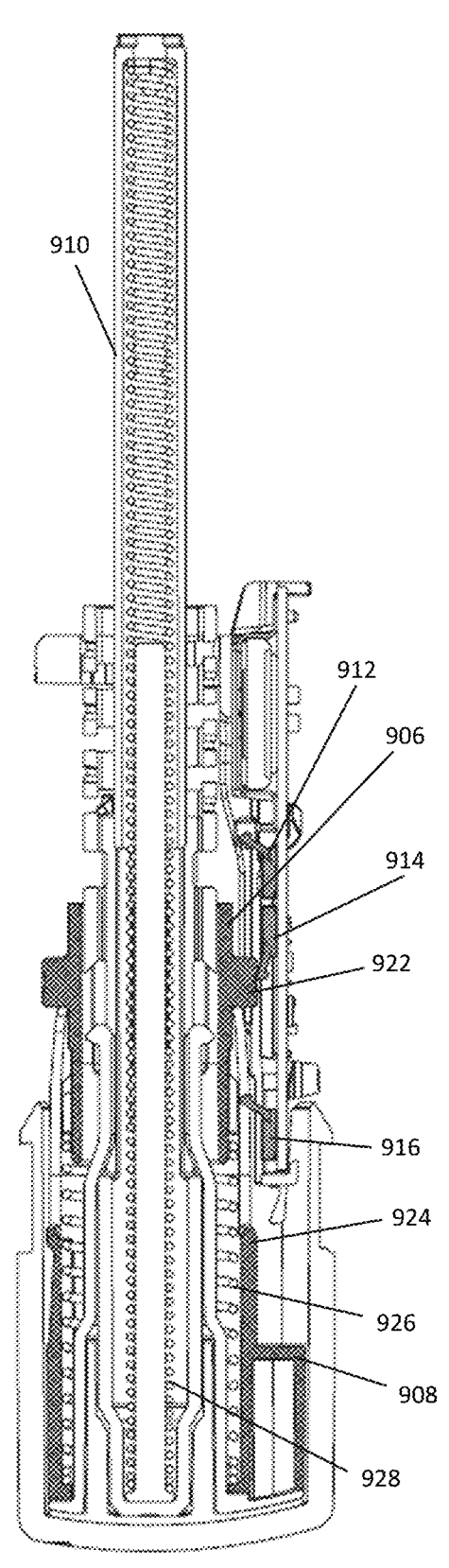

FIG. 9f shows the autoinjector drive module 900 in a delivered state. In the delivered state the drive module 900 is installed into an autoinjector and movement of the plunger rod 910 taking place in FIG. 9e has been substantially completed. Once forward movement of the plunger rod 910 has reached a predetermined position, for example more than 95% of a complete dose delivery, the indicator element 908 is released and is biased rearwards by the trigger spring 926. The trigger element remains in the rearmost position in which the radial projection 922 of the trigger element 906 axially aligned with the second contact switch 914 so that the second contact switch 914 is actuated. In the delivered state the indicator element 908 has been biased backwards so that no portion of the indicator element 908 is axially aligned with the third contact switch 916. As set out above, this change of state of the third contact switches 916 may be recorded as an injector usage event.

Figure 9G:
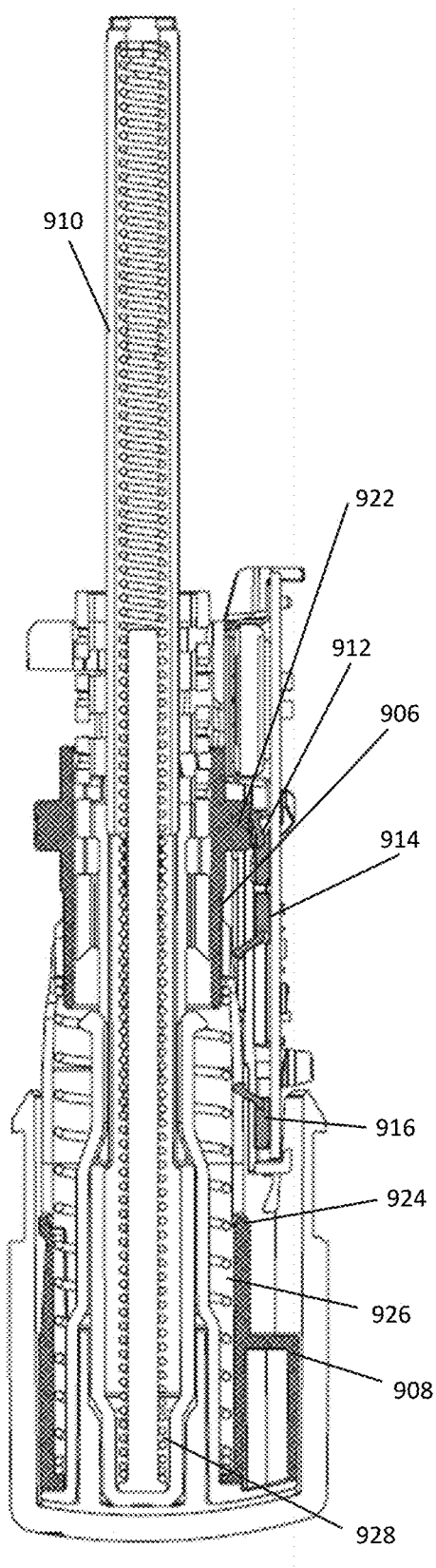

FIG. 9g shows the autoinjector drive module 900 in a used state. In the used state the drive module 900 is installed in an autoinjector, dose delivery has been completed as in FIG. 9f and the autoinjector has been moved away from the skin. The movement of the autoinjector away from the skin allows the needle guard to extend from the autoinjector to a needle protecting position. The forward movement of the needle guard allows the trigger element 906 to move from the rearmost position to the forward position so that the radial projection 922 of the trigger element 906 is axially aligned with, and actuates, the first contact switch 912. In the used state the indicator element 908 has been biased backwards so that no portion of the indicator element 908 is axially aligned with the third contact switch 916. As set out above, this change of state of the first and second contact switches 912,914 may be recorded as an injector usage event. As this is may be considered to be an end of use event entering this state of the switches may trigger the communication module to try to establish communication with a receiving device so that data relating to the recorded usage events can be transmitted to the receiving device once communication has been established. The communication module may to try to establish communication with a receiving device following receipt of trigger signal from the receiving device.

As noted, the description of FIGS. 9a to 9g relate to an example of an autoinjector drive mechanism and its operation. Other drive mechanisms may be used and other detection elements may be employed allowing more or fewer usage events to be recorded during use. A greater number of usage events being recorded, for example in an appropriate sequence may provide a more certain indication of correct autoinjector use.

FIGS. 10a to 10g show views of an example of an autoinjector 1001 having a removable communication module 1002.

Figures 10A, 10B, 10C, 10D:
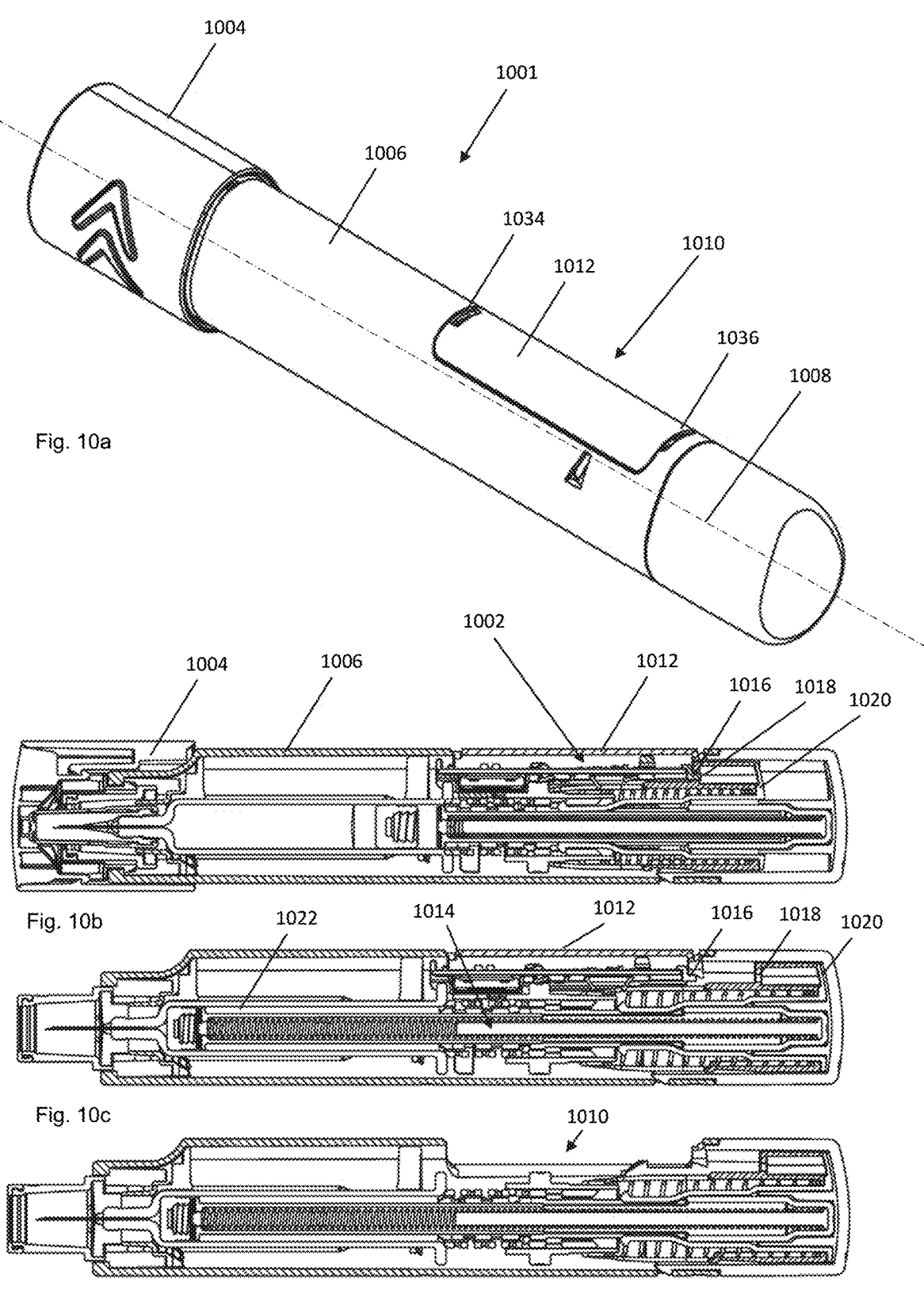
FIG. 10a to 10g show views of an autoinjector with a removable communication module.

FIG. 10a shows an example autoinjector 1001 in a pre-use state in which a cap 1004 is installed on an injection end of the autoinjector 1001. The communication module 1002 is not visible in this figure as it is installed within a housing 1006 of the autoinjector 1001 to provide an integrated device. In this example the autoinjector 1001 is a single use, disposable medicament delivery device and is disposed of following use. To facilitate recycling after the device has been used, the communication module 1002 may be removable from the autoinjector 1001 so that the communication module 1002 and remainder of the autoinjector can be disposed of separately. The housing 1006 extends along a longitudinal axis 1008 of the autoinjector 1001 and comprises an opening 1010 which is covered by a door 1012 which prevents access to an interior of the housing 1006. The door 1012 is held in place at one end by a connector 1034 and at an opposite end by a connector 1036. In this example connector 1034 is a releasable catch which can be actuated to release the door 1012 at that end. In this example connector 1036 is a frangible connector which must be broken to release the door 1012 at that end. In other examples one connector 1034,1036 may be omitted or moved to another location on a periphery of the door 1012, and/or a further connector may be added. One of more connectors may be replaced by a hinge or pivot. In this example both connectors are not the same type, but in other examples both, or all, connectors may be of the same type, either both, or all, releasable, or both, or all, frangible.

FIG. 10b shows a cross section through the example autoinjector 1001 along the longitudinal axis and through the door 1012. In this example the communication module 1002 is arranged adjacent the door 1012 and may be coupled to a drive mechanism 1014 of the autoinjector 1001. In this example a projection 1016 of the communication module 1002 engages in an opening 1018 of an indicator element 1020 of the drive mechanism 1014 to couple the communication module 1002 to a movable element of the drive mechanism 1014. The engagement of the projection 1016 in the opening 1018 may prevent the communication module 1002 being moved in a direction perpendicular to the longitudinal axis 1008 of the autoinjector 1001. It can be seen that the communication module is location in a rear portion of the device 1001, in this case a rear half of the device.

FIG. 10c shows the same cross section as FIG. 10b, but with the autoinjector 1001 in a used state. The cap 1004 has been removed, the drive mechanism 1014 has been activated to drive a plunger rod 1022 to deliver a dose of medicament as previously described. The indicator element 1020 has been driven away from the communication module 1002 which, in example this releases the engagement between the projection 1016 of the communication module 1002 and the opening 1018 of the indicator element 1020. The release of the engagement of the projection 1016 in the opening 1018 now allows the communication module 1002 to be moved in a direction perpendicular to the longitudinal axis 1008 of the autoinjector 1001. However, in this example, access to the communication module 1002 is prevented by the door 1012.

FIG. 10d shows the same cross section as FIG. 10b, but with the example autoinjector 1001 in a separated state in which the door 1012 has been removed to expose the opening 1010 and the communication module 1002 has been accessed and removed via the opening 1010. Removal of the communication module 1002 may be achieved by moving the communication module 1002 substantially perpendicular to the longitudinal axis 1008 through the opening 1010. It should be noted that, in this example, such movement of the communication module would have been prevented by the engagement of the projection 1016 in the opening 1018 of the indicator element 1020 if the autoinjector 1001 had not already been used to dispense a medicament dose.

Figures 10E, 10F, 10G:
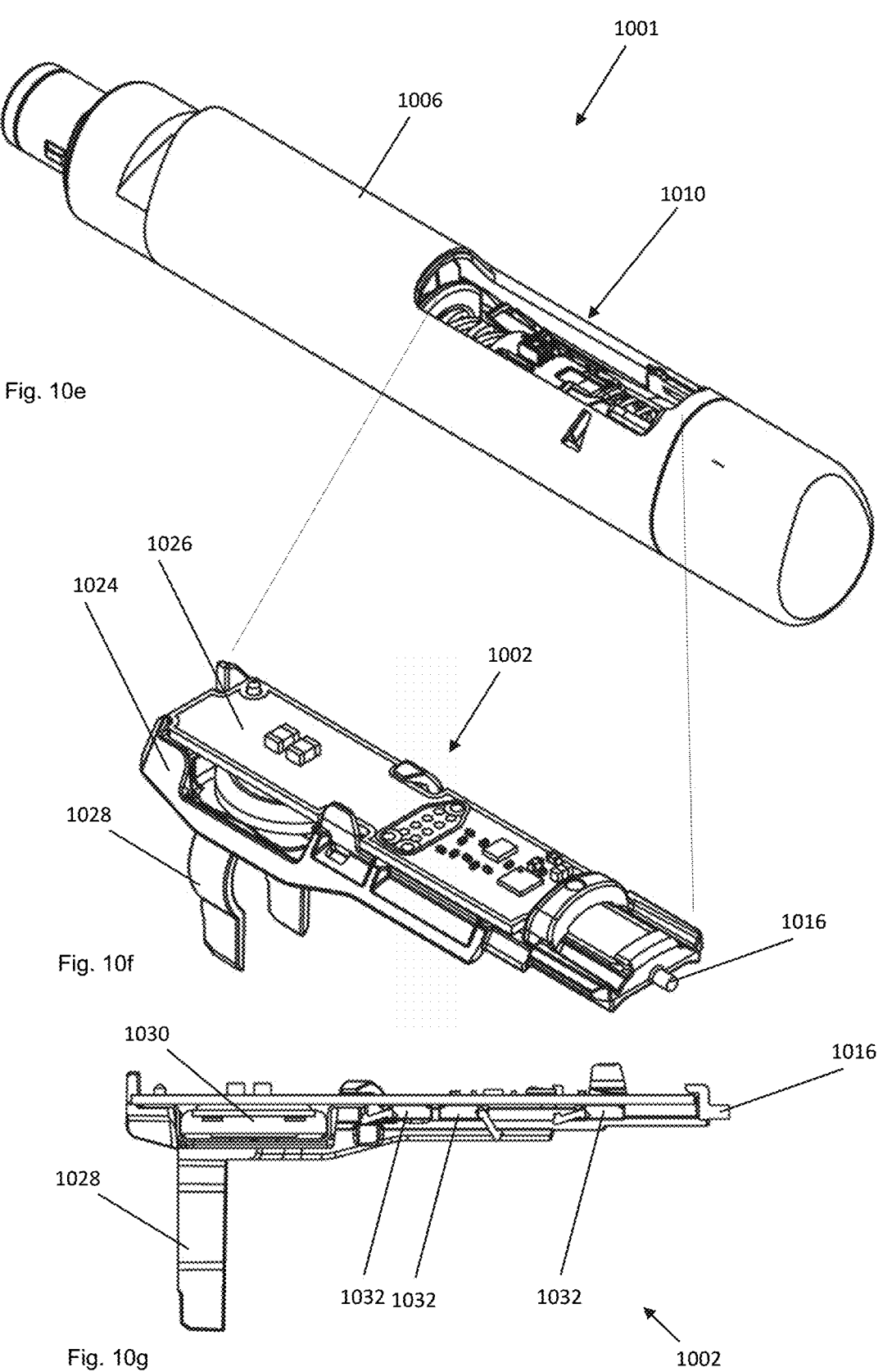

FIGS. 10e and 10f together show a view of the example autoinjector 1001 and the communication module 1002 in the separated state. The communication module 1002 has been removed from the autoinjector 1001 through the opening 1010. The projection 1016 at an end of the communication module 1002 can be clearly seen. The projection 1016 may be formed by any suitable means and from any suitable part of the communication module 1002. In this example the projection 1016 is integrally moulded with a mounting member 1024, which carries a main board 1026 of the communication module 1002 and comprises a c-clip 1028 to couple the communication module 1002 to the drive mechanism 1014. In other examples a different clip and/or projection could be used in the same, or different locations. The projection 1016 could be at an opposite end of the communication module, or at a location between ends of the communication module. In some examples other means of releasably coupling the communication module 1002 to a movable element of the drive mechanism 1014 may be used in addition to, or instead of, the projection 1016. FIG. 10g shows a side view of the communication module 1002 in which a battery 1030 and three contact switches 1032 distributed along the communication module 1002. When the communication module 1002 of this example is installed in the autoinjector 1001 the switches 1032 are arranged in a line parallel with the longitudinal axis of the device 1008.

FIGS. 11a to 11g show views of an example autoinjector 1101 having a removable communication module 1102. The autoinjector 1101 is similar to the autoinjector 1001 and the same numbers incremented by 100 will be used to indicate like parts.

Figures 11A, 11B, 11C, 11D:
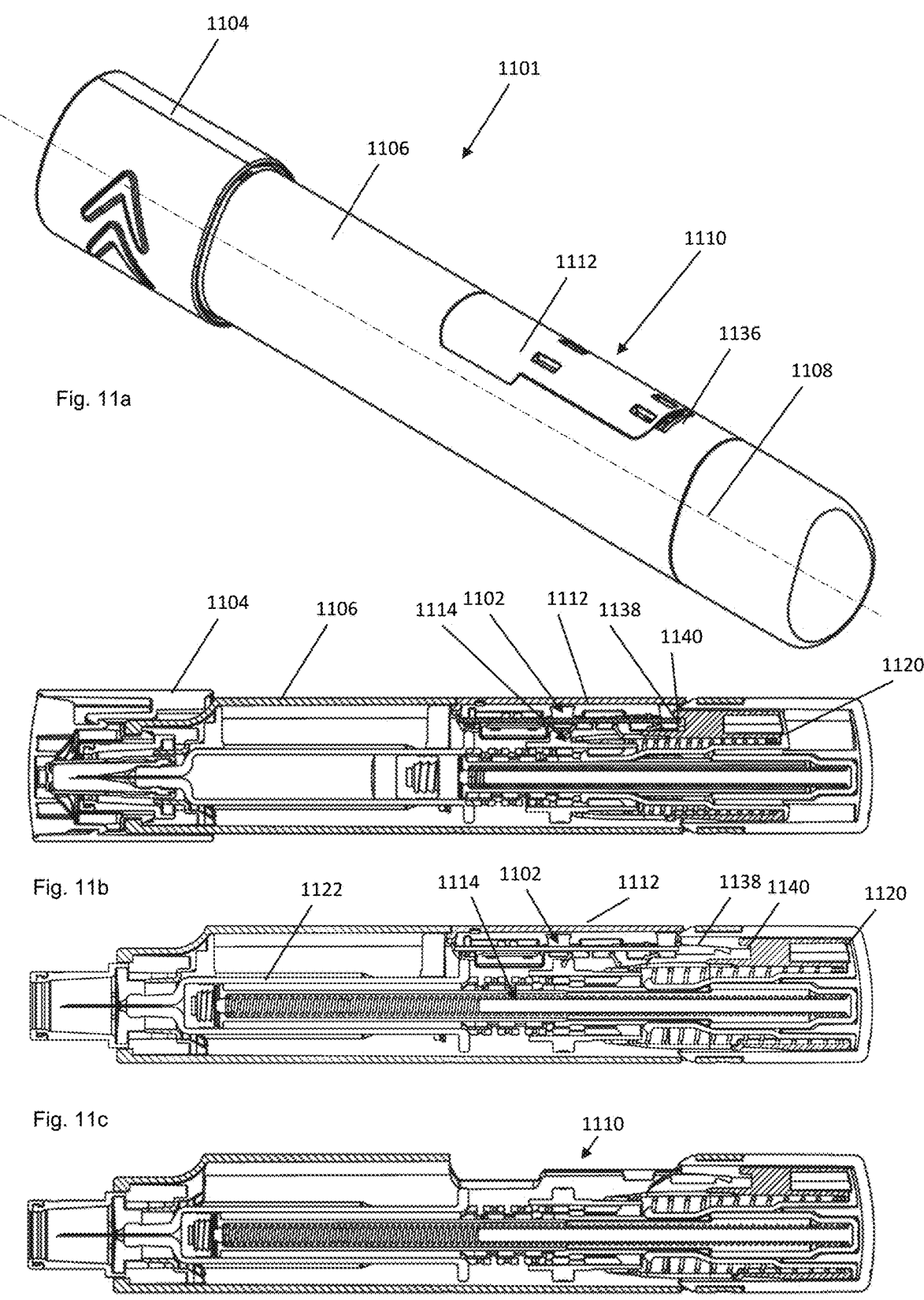
FIGS. 11a to 11g show views of a different autoinjector with a removable communication module.

FIG. 11a shows the example autoinjector 1101 in a pre-use state in which a cap 1104 is installed on an injection end of the autoinjector 1101. The communication module 1102 is not visible in this figure as it is installed within a housing 1106 of the autoinjector 1101. The housing 1106 extends along a longitudinal axis 1108 of the autoinjector 1101 and comprises an opening 1110 which is covered by a door 1112 which prevents access to an interior of the housing 1106.

The door 1112 is held in place at one end by a connector 1136 and at an opposite end by a retainer (not visible in this Figure). Connector 1136 in this example is a snap clip which can be released without breaking, but in other example may be another type of connector, for example a frangible connector which must be broken to release the door 1112 at that end.

This autoinjector 1101 is an example of an autoinjector in which the communication module 1102 may initially be installed into a housing subassembly, such as a housing module, rather than a drive module. The housing module may comprise the communication module and a medicament container. During assembly the communication module 1102 may be removed from the housing 1106 via the opening 1110, the drive mechanism 1114 fitted and then the communication module 1102 then refitted. Some manipulation may be required to engage the communication module 1102 to the drive mechanism 1114, or the communication module 1102 and the drive mechanism 1114 may be adapted to allow automatic engagement, for example by a snap fit or other mechanism.

FIG. 11b shows a cross section through the autoinjector 1101 along the longitudinal axis and through the door 1112. The communication module 1102 is arranged adjacent the door 1112 and is coupled to a drive mechanism 1114 of the autoinjector 1101. Unlike the projection 1016 and opening 1018 of autoinjector 1001 of the previous example, a different engagement between communication module 1102 and indicator element 1120 is provided. In other examples other means of engagement may be used. An extension 1138 of the communication module 1102 engages in a recess 1140 of an indicator element 1120 of the drive mechanism 1114. The engagement of the extension 1138 in the recess 1140 prevents the communication module 1102 being moved in a direction perpendicular to the longitudinal axis 1108 of the autoinjector 1101.

FIG. 11c shows the same cross section as FIG. 11b, but with the autoinjector 1101 in a used state. The cap 1104 has been removed, the drive mechanism 1114 has been activated to drive a plunger rod 1122 to deliver a dose of medicament as previously described. The indicator element 1120 has been driven away from the communication module 1102 thereby releasing the engagement between the extension 1138 of the communication module 1102 and the recess 1140 of the indicator element 1120. As described before, the release of that engagement allows the communication module 1102 to be moved in a direction perpendicular to the longitudinal axis 1108 of the autoinjector 1101. However access to the communication module 1102 is prevented by the door 1112.

FIG. 11d shows the same cross section as FIG. 11b, but with the example autoinjector 1101 in a separated state in which the door 1112 has been removed. In this example the communication module 1102 is attached to the door 1112, so removal of the door 1112 also removes the communication module 1102. Removal of the door 1112 and communication module 1102 is achieved by moving the door 1112 and communication module 1102 substantially perpendicular to the longitudinal axis 1108 so that the communication module 1102 moves through the opening 1110. As discussed before, in this example such movement of the communication module 1102 would have been prevented prior to use of the autoinjector, in this case by the engagement of the extension 1138 in the recess 1140 of the indicator element 1120 of the autoinjector 1101.

Figures 11E, 11F, 11G:
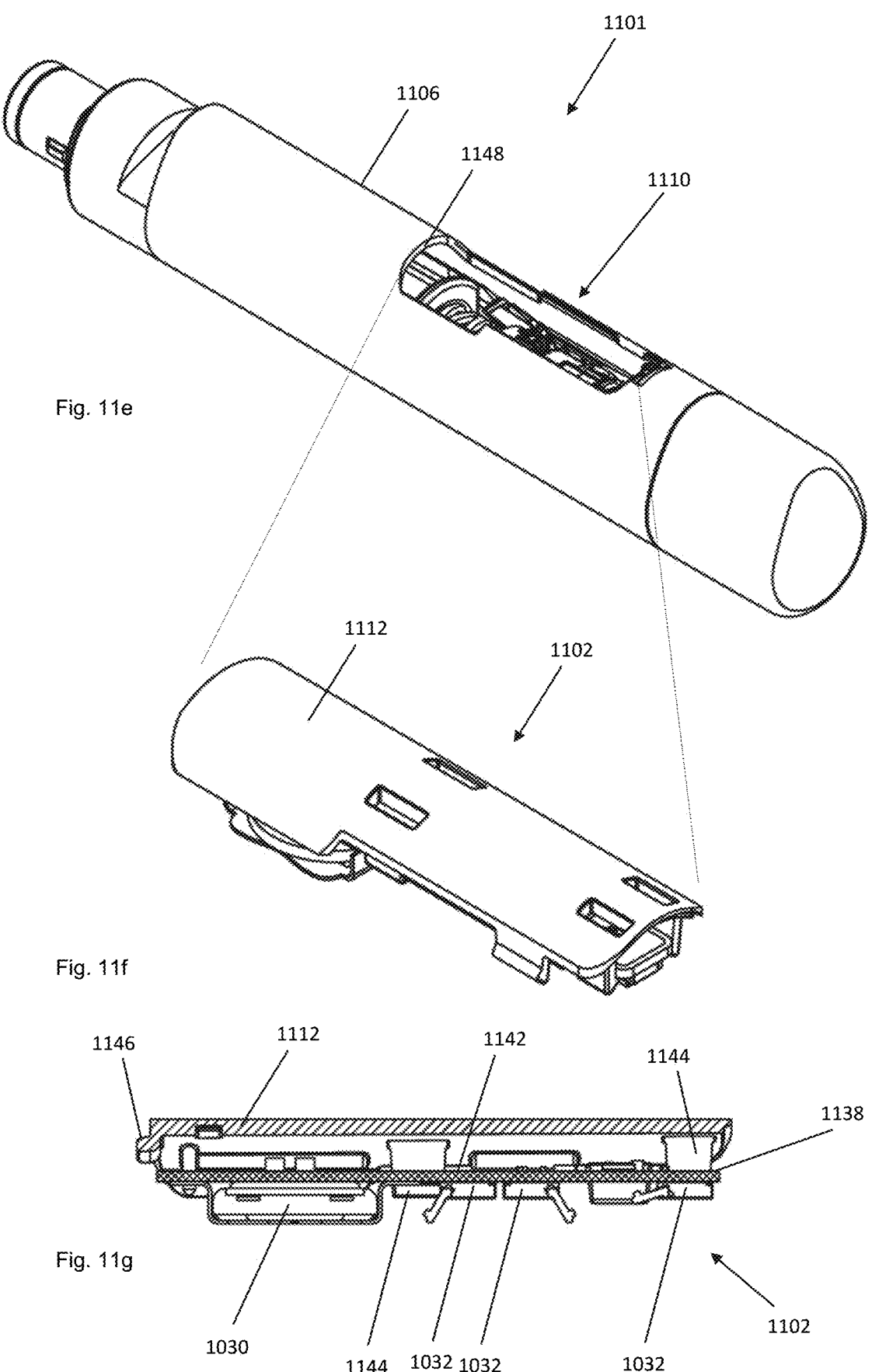

FIGS. 11e and 11f together show a view of the autoinjector 1101 and the communication module 1102 in the separated state. The door 1112 has been removed from the autoinjector 1101 causing the communication module 1102 to be removed from the autoinjector 1101 through the opening 1110. The extension 1138 at an end of the communication module 1102 can be clearly seen. As mentioned in connection with the projection 1016, extension 1038 may be formed by any suitable means and from any suitable part of the communication module 1102. In this example the extension 1138 is part of a main board 1142 of the communication module 1102.

In some examples a removable sticker may be applied covering some or all of the door 1112. After use of the device and completion of data transfer to a receiving device, a user may be instructed to remove the sticker. Removal of the sticker after use of the device may cause the door, and the associated communication module 1102, to be removed from the autoinjector and this may facilitate separation of the communication module from the autoinjector for recycling. The means of holding the door to the housing and/or the means of coupling the communication module to the drive mechanism may be adapted for such use.

FIG. 11g shows a cross section view of the communication module 1102 in which a battery 1130 and three contact switches 1132 distributed along the communication module 1102. The door 1112 is connected to the communication module 1102 by clips 1144 which are integrally molded with the door 1112. The clips 1144 engage with opposed lateral edges of the main board 1142. In this example, when the communication module 1102 and door 1112 is installed in the autoinjector 1101 the switches 1132 are arranged in a line parallel with the longitudinal axis of the device 1108, although other arrangements are possible.

The retainer 1146 which holds an end of the door 1112 opposite the connector 1136 is visible in this figure. The retainer 1146 is in the form of a hook which is adapted to fit under an edge 1148 of the housing 1106 which defines an end of the opening to prevent movement of the door perpendicular to the longitudinal axis 1108. It will be understood that other retainer designs may be used. To remove the door 1112 and associated communication module 1102 the connector 1136 is broken to release the associated end of the door 1112 so that it can be moved away from the autoinjector in a direction perpendicular to the longitudinal axis 1108 so that the door 1112 pivots about the retainer 1146 until the door 1112 and communication module 1102 can be moved parallel with the longitudinal axis 1108 to release the retainer 1146 from the housing.

In FIGS. 10a to 10g and 11a to 11g it is a part of the communication module that is releasably secured to an element of the drive mechanism. In other examples the door may be additionally, or alternatively, be releasably secured to an element of the drive mechanism.

The autoinjectors 701, 1001 and 1101 shown in FIGS. 7a to 7e, 10a to 10g and 11a to 11g may be suitable for use with the drive module and/or the drive mechanism shown in FIGS. 9a to 9g.

Figures 12, 13:
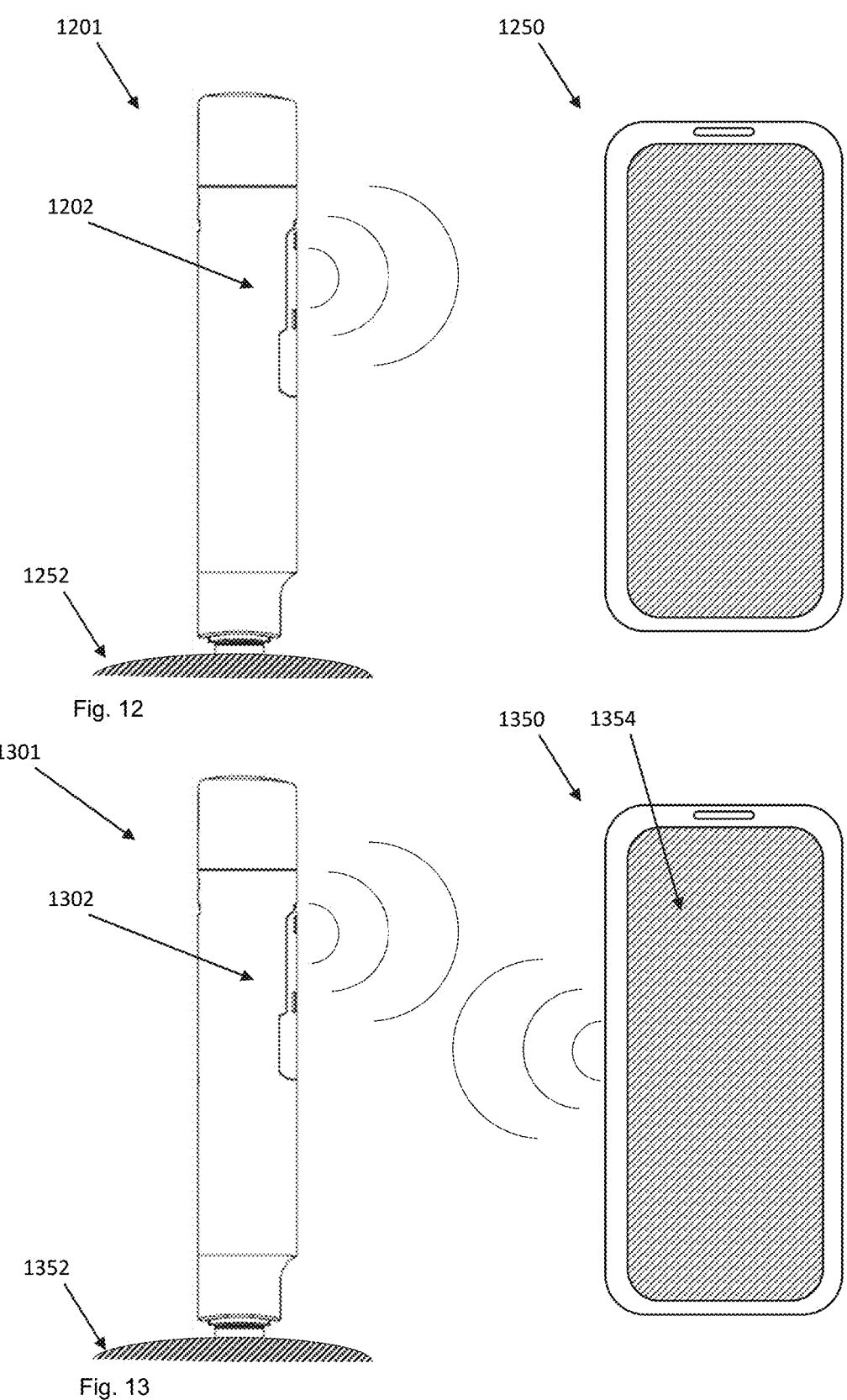
FIG. 12 shows a view of a medicament delivery autoinjector and an associated receiving device.
FIG. 13 shows a view of a training autoinjector and an associated receiving device.

FIG. 12 shows an example of a medicament delivery autoinjector 1201 and an associated receiving device 1250, in this example a smart phone, but in other examples may be any suitable receiving device, including a computing device, tablet, laptop, hub or smart watch.

The receiving device 1250 may be associated with the autoinjector 1201 through any suitable wireless connection, for example wireless software linking or pairing of the two devices to establish one- or two-way communication between the devices, or the communication could be one directional from the autoinjector 1201 to the receiving device 1250 following use, in which case the receiving device 1250 may be regarded as associated as it is able to receive transmissions from the communication module 1202.

During use of the autoinjector 1201, as described above, a user may remove a cap to change the state of a first switch and so enable at least some of the functions of a communication module 1202 housed in the autoinjector 1201. The autoinjector 1201 may then be oriented at a preferred injection angle relative to an injection surface 1252. The orientation may be detected by the communication device 1202.

The autoinjector 1201 may then be pushed against an injection surface 1252 which may cause a needle guard to be pushed back into the autoinjector 1201 and this may change a state of a second switch of the communication module 1202 as described above.

Following completion of medicament delivery an indicator element may be released and may move away from the injection surface 1252 and this may change a state of a third switch of the communication module 1202 as described above.

Removing the autoinjector 1201 from the injection surface 1252 may allow the needle guard to extend from the autoinjector 1201 and this may change a state of a second switch of the communication module 1202 as described above.

Completion of this use cycle may automatically trigger the wireless transmission of data relating to the use of the autoinjector 1201 to the receiving device 1250. In some examples the completion of this use cycle may trigger the communication module 1202 to store data relating to the use of the autoinjector 1201 for later transmission to the receiving device 1250. Transmission of the data to the receiving device 1250 may occur following a request from the receiving device 1250 which may be received wirelessly by a receiver of the communication module 1202. The receiver of the communication module 1202 may be integrated with the transmitter of the communication module 1202 in the form of a transceiver.

Following completion of the injection, the communication module may be separated from the autoinjector, for example as described with reference to FIGS. 10a to 10g or 11a to 11g. The separation of the communication module from the autoinjector may take place after completion of the transmission of data, or may take place prior to transmission of the data, FIG. 13 shows a training autoinjector 1301, in this case the training autoinjector is also a medicament delivery device, but in other examples may not be, and an associated receiving device 1350, in this example, as above, a smart phone, but in other examples may be any suitable receiving device, including a computing device, tablet, laptop, hub or smart watch.

As described above, the receiving device 1350 may be associated with the autoinjector 1301 through any suitable wireless connection, for example wireless software linking or pairing of the two devices to establish one- or two-way communication between the devices, or the communication could be one directional from the autoinjector 1301 to the receiving device 1350 following use, in which case the receiving device 1350 may be regarded as associated as it is able to receive transmissions from the communication module 1302.

During use of the autoinjector 1301, as described above, a user may remove a cap to change the state of a first switch and so enable at least some of the functions of a communication module 1302 housed in the autoinjector 1301. This may initiate communication between the receiving device 1350 and the communication module 1302. During use of the training device 1301 there may be wireless communication established between the receiving device 1350 and the autoinjector 1301. The receiving device 1350 may include a screen 1354, or other feedback device, for example a microphone or tactile feedback generator, and may display information relating to the state of the autoinjector 1301 based, for example on detected usage events, for example confirming that a cap has been removed.

The autoinjector 1301 may then be oriented at a preferred injection angle relative to an injection surface 1352. The orientation may be detected by the communication device 1302 and displayed on the receiving device 1350. The receiving device may include an indication regarding whether or not the autoinjector 1301 is in an appropriate orientation to begin an injection event.

The autoinjector 1301 may then be pushed against an injection surface 1352 which may cause a needle guard to be pushed back into the autoinjector 1301 and this may change a state of a second switch of the communication module 1202 as described above. The change in state of the autoinjector 1301 may be indicated on the receiving device 1350.

Following completion of medicament delivery an indicator element may be released and may move away from the injection surface 1352 and this may change a state of a third switch of the communication module 1302 as described above. The change in state of the autoinjector 1301 may be indicated on the receiving device 1350.

Removing the autoinjector 1301 from the injection surface 1352 may allow the needle guard to extend from the autoinjector 1301 and this may change a state of a second switch of the communication module 1302 as described above. The change in state of the autoinjector 1301 may be indicated on the receiving device 1350.

In some examples an animation or other visual representation of the state of the autoinjector may be displayed on the receiving device to inform and/or guide a user during use of the autoinjector.

Completion of this use cycle may trigger a use summary to be displayed on the receiving device 1350, for example confirming that the device was maintained in an appropriate orientation during an injection event and that the device was maintained in position against the injection surface for a length of time sufficient for medicament delivery to be completed. The receiving device may provide suggestions for improvements for subsequent use of the autoinjector 1301.

It should also be noted that indications regarding the state of the autoinjector 1301 may be displayed, or provided, additionally or alternatively on the autoinjector 1301, for example on a display, or via one or more lights, or via audible or tactile feedback. Such an indication may be the result of a wireless signal from the receiving device 1350.

Following completion of the injection, the communication module may be separated from the autoinjector, for example as described with reference to FIGS. 10a to 10g or 11a to 11g.

The invention claimed is:

1. Communication module for an autoinjector comprising:
   a. a detector component configured to detect an injector usage event to obtain injector usage information, and
   b. a transmitter component configured to wirelessly transmit the injector usage information to a receiving device, and
   c. a main board comprising a printed circuit board to which components of the communication module are attached, a power source for powering the communication module, and a processor configured to process an injector usage signal to detect an injector usage event, the main board comprising at least one component having a memory, the detector component comprising at least one contact switch positioned along a first axis of the communication module, wherein operating states of the at least one contact switch are indicative of a state of the autoinjector, wherein the at least one contact switch comprises three contact switches distributed along the first axis of the communication module.

2. Communication module according to claim 1, the communication module having a low power mode in which the detector component is configured to detect removal of a cap of the autoinjector and, upon detection of the removal of a cap of the autoinjector, to change the communication module from the low power mode to a use mode by enabling one or more elements of the communication module enabling detection of further injector usage events and/or data transmission.

3. Communication module according to claim 1, wherein the detector component is configured to detect electrical, magnetic, acoustical, optical, orientation and/or acceleration signals and is configured obtain an injector usage signal upon detection of an injector usage event.

4. Communication module according to claim 1, wherein the injector usage event is one of:
   a. an injection preparatory event including at least one of uncasing the autoinjector or removal of a cap of the autoinjector, and
   b. an injection event including at least one of placement of the autoinjector onto an injection site, start of movement of an injection needle towards puncture, start of dispensing a fluid product, completion of dispensing a fluid product, or removal of the autoinjector from an injection site.

5. Communication module according to claim 1, wherein the transmitter component is configured for transmission via Bluetooth, WLAN, LPWAN, RFID or mobile communications network.

6. Communication module according to claim 1, comprising a battery for powering the detector component and/or the transmitter component and an activation mechanism to activate the detector component and/or the transmitter component.

7. Drive module for an autoinjector, the drive module comprising a drive mechanism and a communication module comprising:
   a. a detector component configured to detect an injector usage event to obtain injector usage information, and
   b. a transmitter component configured to wirelessly transmit the injector usage information to a receiving device,
   the drive mechanism including a trigger element which is movable to control an operation of the drive mechanism, and the detector component including at least one contact switch arranged to contact the trigger element as the trigger element moves during an operation of the drive mechanism, the at least one contact switch comprising a first contact switch to contact the trigger element in a forward position, and a second contact switch to contact the trigger element in a rearmost position.

8. Drive module according to claim 7, wherein the drive mechanism includes an indicator element which is movable to indicate a state of operation of the drive mechanism, and wherein the detector component includes at least one contact switch arranged to contact the indicator element as the indicator element moves during an operation of the drive mechanism.

9. Drive module according to claim 8, wherein the at least one contact switch is arranged to contact the indicator element in an initial position, and not in an indication position.

10. Drive module for an autoinjector, the drive module comprising a drive mechanism and a communication module comprising:
   a. a detector component configured to detect an injector usage event to obtain injector usage information, and

b. a transmitter component configured to wirelessly transmit the injector usage information to a receiving device, wherein at least a portion of the communication module is releasably secured to a component of the drive mechanism, the component of the drive mechanism securing the communication module to the drive mechanism when in an initial position prior to use of the drive mechanism and the component of the drive mechanism moving during use of the drive mechanism to release at least the portion of the communication module, wherein the communication module comprises a main board, the main board comprising a board feature, and wherein the component of the drive mechanism includes a component feature which, when engaged with the board feature, secures the communication module to the drive mechanism, the component of the drive mechanism moving during use of the drive mechanism to move the component feature out of engagement with the board feature.

11. Drive module according to claim 10, wherein the component of the drive mechanism including the component feature is an indicator element which is movable to indicate a state of operation of the drive mechanism.

12. Autoinjector comprising a drive module comprising a drive mechanism and a communication module comprising:

a. a detector component configured to detect an injector usage event to obtain injector usage information, and b. a transmitter component configured to wirelessly transmit the injector usage information to a receiving device, wherein the communication module is mounted within a housing of the autoinjector such that the communication module is disposed entirely within an interior of the housing,

wherein at least a portion of the communication module is releasably secured to a component of a drive mechanism of the autoinjector, the component of the drive mechanism being configured to secure the communication module to the drive mechanism when in an initial position prior to use of the drive mechanism and being configured to move during use of the drive mechanism to release at least the portion of the communication module.

13. Autoinjector according to claim 12, wherein the communication module is located so that the communication module is removable via an opening in a wall of the autoinjector housing, and wherein the opening in the housing is covered by a moveable portion.

14. Autoinjector comprising a drive module comprising a drive mechanism and a communication module comprising:

a. a detector component configured to detect an injector usage event to obtain injector usage information, and b. a transmitter component configured to wirelessly transmit the injector usage information to a receiving device, wherein the communication module is mounted within a housing of the autoinjector, wherein at least a portion of the communication module is releasably secured to a component of a drive mechanism of the autoinjector, the component of the drive mechanism securing the communication module to the drive mechanism when in an initial position prior to use of the drive mechanism and moving during use of the drive mechanism to release at least the portion of the communication module.

* * * * *